United States Patent
Dehghanpoor et al.

(10) Patent No.: US 12,175,354 B1
(45) Date of Patent: Dec. 24, 2024

(54) APPARATUS AND METHOD FOR TRAINING A TUNABLE DATA STRUCTURE TO PREDICT INTERNAL RIBOSOME ENTRY SITE (IRES) ACTIVITY

(71) Applicant: Orna Therapeutics, Inc., Watertown, MA (US)

(72) Inventors: Ramin Dehghanpoor, Medford, MA (US); Varun Shivashankar, Cambridge, MA (US)

(73) Assignee: Orna Therapeutics, Inc., Watertown, MA (US)

( * ) Notice: Subject to any disclaimer, the term of this patent is extended or adjusted under 35 U.S.C. 154(b) by 0 days.

(21) Appl. No.: 18/601,269

(22) Filed: Mar. 11, 2024

(51) Int. Cl.
| | |
|---|---|
| *G16B 20/20* | (2019.01) |
| *G06N 3/0455* | (2023.01) |
| *G06N 5/01* | (2023.01) |
| *G16B 5/10* | (2019.01) |
| *G16B 15/10* | (2019.01) |
| *G16B 35/10* | (2019.01) |

(Continued)

(52) U.S. Cl.
CPC .............. *G06N 3/0455* (2023.01); *G16B 5/10* (2019.02); *G16B 15/10* (2019.02); *G16B 40/20* (2019.02)

(58) Field of Classification Search
CPC ........ G06N 3/0455; G16B 5/10; G16B 15/10; G16B 40/20
See application file for complete search history.

(56) References Cited

U.S. PATENT DOCUMENTS

| | | |
|---|---|---|
| 11,398,297 B2 | 7/2022 | Chang |
| 2021/0261949 A1* | 8/2021 | Serber .................. G01N 35/10 |

(Continued)

FOREIGN PATENT DOCUMENTS

| | | |
|---|---|---|
| CN | 116525001 A | 8/2023 |
| WO | 2023197718 A1 | 10/2023 |
| WO | 2023225221 A1 | 11/2023 |

OTHER PUBLICATIONS

Chen et al; iLearnPlus: a comprehensive and automated machine-learning platform for nucleic acid and protein sequence analysis, prediction and visualization; Nucleic Acids Research, vol. 49, Issue 10, Jun. 4, 2021, p. e60, Published: Feb. 28, 2021.

(Continued)

*Primary Examiner* — Brandon S Cole
(74) *Attorney, Agent, or Firm* — Caldwell Intellectual Property Law

(57) ABSTRACT

An apparatus for training a tunable data structure to predict internal ribosome entry site (IRES) activity includes at least a processor and a memory containing instructions configuring the at least a processor to assemble a training set including a plurality of nucleotide sequence data examples IRES sequences and a plurality of correlated observed IRES activity, partition the training set into at least a first section and a second section, train, using the first section at least an activity data structure to generate probable IRES activity using nucleotide sequence data, and iteratively retrain the at least an activity data structure using the second section, wherein each iteration of the iterative retraining includes generating a predicted IRES activity value using the at least an activity neural network and a nucleotide sequence data example, evaluating an error function, and tuning the activity data structure.

16 Claims, 10 Drawing Sheets

(51) Int. Cl.
*G16B 40/20* (2019.01)
*G16B 40/30* (2019.01)

(56) References Cited

U.S. PATENT DOCUMENTS

| | | | |
|---|---|---|---|
| 2022/0180975 A1* | 6/2022 | Regev | G16B 40/20 |
| 2022/0300711 A1* | 9/2022 | Elisco | G06F 16/93 |
| 2023/0070049 A1* | 3/2023 | Junn | C12N 15/86 |
| 2023/0116385 A1* | 4/2023 | Nagpal | G16B 35/10 |
| | | | 424/499 |
| 2023/0402127 A1 | 12/2023 | Altman et al. | |

OTHER PUBLICATIONS

Jacob Schreiber et al; Avocado: a multi-scale deep tensor factorization method learns a latent representation of the human epigenome; Genome Biology vol. 21, Article No. 81 (2020) Published: Mar. 30, 2020.

* cited by examiner

APPARATUS AND METHOD FOR TRAINING A TUNABLE DATA STRUCTURE TO PREDICT INTERNAL RIBOSOME ENTRY SITE (IRES) ACTIVITY

FIELD OF THE INVENTION

The present invention generally relates to the field of artificial intelligence and machine learning. In particular, the present invention is directed to an apparatus and method for training a tunable data structure to predict internal ribosome entry site (IRES) activity.

BACKGROUND

Ribonucleic acid (RNA) interacts with other biological elements such as ribosomes in various complex ways that science has only recently begun to appreciate. Of particular interest are the various sequences and structures that can give RNA, whether cellular mRNA, viral RNA, or other structures, access to a ribosome to begin translation. Although the list of such elements continues to grow, their relative efficacy has proven difficult to determine using current automated systems.

SUMMARY OF THE DISCLOSURE

In an aspect, an apparatus for training a tunable data structure to predict internal ribosome entry site (IRES) activity includes at least a processor and a memory communicatively connected to the at least a processor, the memory containing instructions configuring the at least a processor to assemble a training set, the training set comprising a plurality of nucleotide sequence data examples describing a plurality of IRES sequences and a plurality of correlated observed IRES activity, partition the training set into at least a first section and a second section, train, using the first section at least an activity data structure to generate probability of IRES activity using nucleotide sequence data, and iteratively retrain the at least an activity data structure using the second section, wherein each iteration of the iterative retraining includes generating a predicted IRES activity value using the at least an activity neural network and a nucleotide sequence data example, evaluating an error function using the predicted IRES activity value and an observed IRES activity correlated to the nucleotide sequence data example, and tuning the at least an activity data structure using the evaluated error function.

In another aspect a method of training a tunable data structure to predict internal ribosome entry site (IRES) activity includes assembling, by a computing device, a training set, the training set comprising a plurality of nucleotide sequence data examples describing a plurality of IRES sequences and a plurality of correlated observed IRES activity, partitioning the training set into at least a first section and a second section, training, using the first section, at least an activity data structure to generate probable IRES activity using nucleotide sequence data, and iteratively retraining the at least an activity data structure using the second section, wherein each iteration of the iterative retraining further includes generating a predicted IRES activity value using the at least an activity neural network and a nucleotide sequence data example, evaluating an error function using the predicted IRES activity value and an observed IRES activity correlated to the nucleotide sequence data example, and tuning the at least an activity data structure using the evaluated error function.

In another aspect a non-transitory machine-readable medium contains instructions configured to cause at least a processor to assemble a training set, the training set comprising a plurality of nucleotide sequence data examples describing a plurality of IRES sequences and a plurality of correlated observed IRES activity, partition the training set into at least a first section and a second section, train at least an activity data structure to generate probable IRES activity using nucleotide sequence data, and iteratively retrain the at least an activity data structure using the second section, wherein each iteration of the iterative retraining further includes generating a predicted IRES activity value using the at least an activity neural network and a nucleotide sequence data example, evaluating an error function using the predicted IRES activity value and an observed IRES activity correlated to the nucleotide sequence data example, and tuning the at least an activity data structure using the evaluated error function.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments herein train a tunable data structure, which may include one or more neural networks, to predict activity of IRES using partitioned training sets. Training examples may include representations of nucleotide sequences including embodiments encoding one or more sequential, structural, and/or other physical and/or statistical attributes of sequences. Windowed aggregation of embeddings may be used to represent long sequences. Training may include pretraining and tuning stages using different sections of partitioned training sets.

Figure 1:
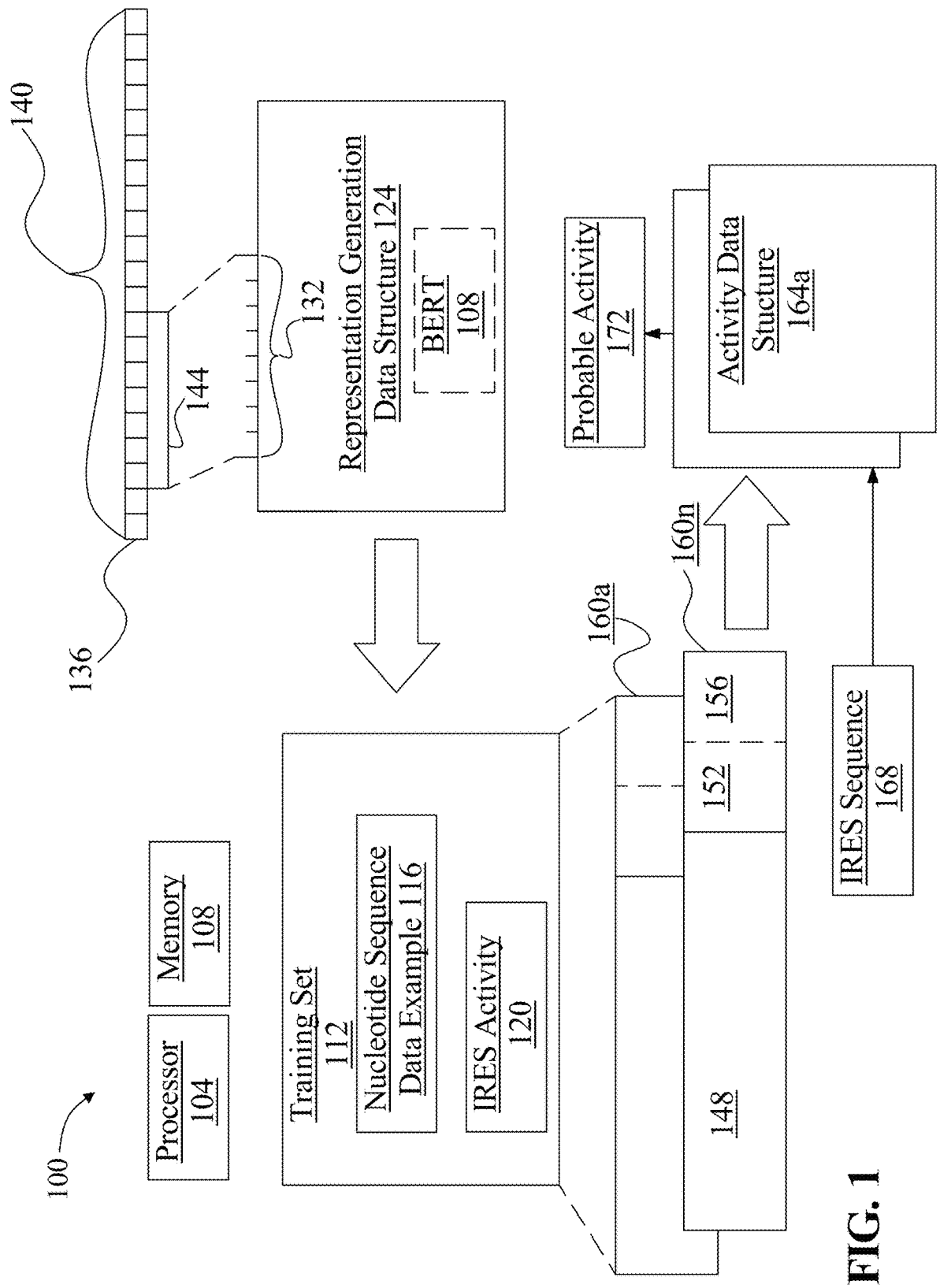
FIG. 1 is block diagram illustrating an exemplary embodiment of an apparatus for training a tunable data structure to predict internal ribosome entry sites (IRES) activity.

Referring now to FIG. 1, an exemplary embodiment of an apparatus 100 for training a tunable data structure to predict internal ribosome entry site (IRES) activity is illustrated. Apparatus 100 may include a computing device. Apparatus 100 includes a processor 104 communicatively connected to a memory 108. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, apparatus 100 may include any computing device as described in this disclosure, including without limitation a microcontroller, microprocessor, digital signal processor (DSP) and/or system on a chip (SoC) as described in this disclosure. Apparatus 100 may include, be included in, and/or communicate with a mobile device such as a mobile telephone or smartphone. Apparatus 100 may include a single computing device operating independently, or may include two or more computing device operating in concert, in parallel, sequentially or the like; two or more computing devices may be included together in a single computing device or in two or more computing devices. Apparatus 100 may interface or communicate with one or more additional devices as described below in further detail via a network interface device. Network interface device may be utilized for connecting apparatus 100 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Apparatus 100 may include but is not limited to, for example, a computing device or cluster of computing devices in a first location and a second computing device or cluster of computing devices in a second location. Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory 108 between computing devices. Apparatus 100 may be implemented, as a non-limiting example, using a "shared nothing" architecture.

With continued reference to FIG. 1, apparatus 100 may be designed and/or configured to perform any method, method step, or sequence of method steps in any embodiment described in this disclosure, in any order and with any degree of repetition. For instance, apparatus 100 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Apparatus 100 may perform any step or sequence of steps as described in this disclosure in parallel, such as simultaneously and/or substantially simultaneously performing a step two or more times using two or more parallel threads, processor 104 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, memory 108 contains instructions configuring at least a processor 104 to assemble a training set 112. Training set 112 may include training data, for instance and without limitation as described in further detail below. Training set 112 includes a plurality of nucleotide sequence data examples 116 describing a plurality of IRES sequences 160 and a plurality of correlated observed IRES activity 120. An element of "nucleotide sequence data" and/or a "nucleotide sequence data example 116," as used in this disclosure, is an element of data and/or data structure representing a nucleotide sequence. A "nucleotide sequence," as used in this disclosure, is a chemical compound including two or more nucleotides attached together sequentially. Nucleotides may include any nucleotides of RNA or deoxyribonucleic acid (DNA), such as adenine, thymine, guanine, cytosine, or uracil; such nucleotides may be connected in sequence by covalent bonds in a phosphate backbone to form DNA, RNA, or the like. Alternatively or additionally a nucleotide sequence may include a peptide nucleic acid, defined as a DNA and/or RNA analog having a peptide backbone formed, for instance, from a (2-aminoethyl) glycine carbonyl unit, as opposed to a phosphate backbone, that is linked to a nucleotide base by a glycine amino nitrogen and/or methylene linker.

Still referring to FIG. 1, a nucleic acid sequence may include DNA. DNA may include a plurality of deoxyribonucleotides that may include adenine, thymine, guanine, and/or cytosine linked by a phosphate backbone. Such nucleotide sequences may be isolated or formed into a double helix with a second nucleotide sequence of complementary nucleotides forming base pairs.

With further reference to FIG. 1, a nucleic acid sequence may include RNA. RNA may include a plurality of ribonucleotides that may include adenine, cytosine, guanine, and/or uracil connected together using a phosphate backbone. RNA may include, without limitation, transfer RNA (tRNA), messenger RNA (mRNA), viral RNA, and/or circular RNA (ORNA). ORNA is defined for the purposes of this disclosure as a strand of RNA that has been joined at its ends, forming a continuous loop; this may be performed using an enzyme and/or an RNA sequence having a property of "self-circularization," wherein strand ends are so formed and/or constructed as to connect or fuse together naturally into a circular structure.

Still referring to FIG. 1, RNA may fold and/or form electrostatic bonds, hydrogen bonds, and/or base-pair interactions between nucleotides to form secondary structures. Secondary structures may take on various forms, such as stem-loop structures (which may also be referred to as a "hairpin"), in which a base-paired helix and/or ladder ends in a short loop of unpaired nucleotides. Stem-loop structures may combine to form larger structures of RNA. Examples of stem-loop structures include RHO-independent terminator stem-loops, tRNA cloverleaf structures, or the like. Secondary structures may include pseudoknots. A pseudoknot may include a nucleic acid secondary structure containing at least two stem-loop structures in which half of one stem is intercalated between the two halves of another stem. Pseudoknots may fold into knot-shaped three-dimensional conformations but may not form true topological knots. Secondary structures may further include helical duplexes, triple-stranded structures, and other components, and any combination of secondary structure elements as described above may combine into various forms; persons skilled in the art, upon reviewing the entirety of this disclosure, will be aware of various combinations of secondary structure elements that may be formed.

With continued reference to FIG. 1, RNA may alternatively or additionally form tertiary structures. For the purposes of this disclosure, an RNA tertiary structure is defined as the three-dimensional arrangement of RNA building blocks, which include helical duplexes, triple-stranded structures, and other components that are held together through connections collectively termed RNA tertiary interactions. RNA tertiary structures may include, without limitation, double-helices, major and minor groove triplexes, quadruplexes, coaxial stacking, tetraloop-receptor interactions, A-minor motifs, and/or ribose zippers. Persons skilled in the art, upon reviewing the entirety of this disclosure, will be aware of various potential RNA tertiary structures that may form. In some embodiments, secondary and/or tertiary structures may affect behavior of RNA, including IRES activity 120; as described in further detail below, structures may be entered explicitly into models and/or training examples, and/or may be learned and/or embedded through latent space, learned RNA representations, or the like.

Still referring to FIG. 1, nucleotide sequence may include an IRES sequence, defined for the purposes of this disclosure as a sequence of RNA that is identified as including an IRES. An IRES sequence may, in a non-limiting example, be included in an RNA sequence, e.g., a circular RNA or oRNA®, that combines a IRES with (e.g., operably linked to) one or more coding or other sequential elements suitable to produce peptides, oligomers, and/or proteins, or otherwise to perform therapeutic or other results within target and/or host cells. As used in this disclosure, an "IRES" refers to an RNA sequence or structural element ranging in size from 10 nt to 1000 nt or more, capable of initiating translation of a polypeptide in the absence of a typical RNA cap structure. In some embodiments, the IRES is capable of initiating and/or promoting translation of an RNA, e.g., from a ribosome. An exemplary IRES can be about 500 nt to about 700 nt in length. In an embodiment, different IRES may have different degrees to which translation is promoted and/or different probabilities of initiating translation. A probability of initiating translation in a ribosome by a given IRES is defined as the "activity" of that IRES; an IRES with higher activity is more likely to initiate translation, including in the absence of promoter chemicals, peptides, proteins or the like, and thus will more frequently cause generation of peptides, oligomers, proteins, or the like when introduced host and/or target cells. An effect of an IRES may be dictated and/or enhanced, without limitation, by a particular sequence of nucleotides, a secondary structure formed thereby, and/or by a tertiary structure thereof. A given IRES may have a probability of activity, or in other words of entry into a ribosome and/or causing translation of sequences attached to the given IRES; in some embodiments, methods and/or apparatuses described herein may be configured to and/or have the result of predicting and/or determining a probability that a given IRES will enter a ribosome, and/or an aggregate probability, probability density of entry events and/or frequency of a plurality of sequences with a given IRES or the like. This may include a possibility that some proportion of RNA molecules with a given IRES will successfully be translated, leading to a degree of expression in the aggregate. Alternatively or additionally, probability may include a probability that a given RNA molecule containing a given IRES will be expressed at all or will not be expressed at all.

With continued reference to FIG. 1, although this disclosure describes use of apparatus 100 elements and/or components, system components, and/or method steps to determine activity of IRES, embodiments described herein should not be considered as limited in applicability to analysis and/or classification of IRES. Apparatus 100 elements and/or components, system components, and/or method steps may also be applied to determine activity of alternative or additional coding and/or non-coding nucleotide sequences, generate representations and/or encodings thereof, and/or otherwise perform analytical tasks with regard to such sequences.

Still referring to FIG. 1, in some embodiments, assembling training data may include encoding a representation of secondary and/or tertiary structures in and/or with nucleotide sequence data examples 116. In some embodiments, secondary and/or tertiary structures associated with a nucleotide sequence may be known and/or previously determined. Alternatively or additionally, a model such as a machine-learning model and/or neural network may be trained to predict secondary and/or tertiary structures of a nucleotide sequence from the sequence itself. Apparatus 100 may perform training and/or may receive machine-learning model and/or neural network from a remote device; apparatus 100 may instantiate a previously trained machine-learning model and/or neural network. Training data to train a machine-learning model and/or neural network to predict secondary and/or tertiary structures may include a plurality of sequence examples correlated with experimentally determined and/or user-predicted secondary and/or tertiary structures. Model to be trained may be structured, pre-trained, and/or trained using any methods and/or data structures described in this disclosure and/or that may occur to a person skilled in the art upon reviewing the entirety of this disclosure.

Further referring to FIG. 1, assembling training set 112 may additionally include encoding secondary and/or tertiary structures. For instance, and without limitation, apparatus 100 may convert information describing secondary and/or tertiary structures into dot-bracket form. In an embodiment, a pseudoknot-free secondary structure may be represented a sequence of dots and brackets where the dots represent unpaired bases and the matching brackets represent base pairs, for instance and without limitation as described in further detail below. Dot-bracket notation may be recorded and/or represented for input to one or more data structures, models, and/or neural networks using, for instance, one-hot or other binary encoding for each of the three possible values of ".", "(", and ")". Alternatively or additionally, one or more processes may be used to encode further information concerning a sequence and/or secondary or tertiary structure, such as a base-pair probability in secondary or tertiary structure, a Shannon entropy for base-pairs, kmers as described in further detail, or the like, or any other metric, count, or the like that may be included in an embedding. In some embodiments, two or more of the above encodings may be concatenated to form a larger matrix and/or vector, or may be aggregated in any other way, for a combined input to a data structure, model, and/or neural network as described in further detail below.

Alternatively or additionally, and still referring to FIG. 1, information about secondary and/or tertiary structures of RNA may be, for instance, recorded as a graph, wherein, for instance, individual nucleotides and/or individual secondary structures may be encoded as nodes and different types of bonds from such individual nucleotides to other individual nucleotides may be encoded as edge data. A graph may be produced, without limitation, using a tool such as the Forgi library promulgated by the Python Software Foundation of Beaverton, OR. Secondary structures may be represented in a graph, without limitation, as described below; such graph may be represented, without limitation, using one or more embeddings for input into a neural network and/or other data structure. Metrics to be encoded in graphs and/or node graph embeddings may include, without limitation, secondary structure element (SSE) type, which may indicate the type of secondary structure being represented, SSE sequence, which may include a nucleotide sequence making up a secondary structure represented by a node, and/or kmer counts, which may enumerate a number of each distinct subsequence of k nucleotides in length found in the secondary structure; for instance where k is 3, all AGC subsequences may be counted, all AGU sequences may be counted, and the like.

Still referring to FIG. 1, some embodiments may include use and/or manipulation of kmer-counts, as described herein, in embodiments of methods, apparatuses, and/or instructions described in this disclosure that involve kmer counts, a "kmer count" is defined as a frequency or occurrence of all possible subsequences of length k within a given sequence. In some cases, sequence may include a plurality of MIRES sequences as described herein, or any nucleotide sequences. In some cases, value of k may include 1, 2, 3, 4, 5, or the like. In an embodiment, smaller k value may not capture desired patterns (due to high occurrence in random sequences), while higher k value may be too specific and sparse (especially in shorter sequences or sequences with high variability). As a non-limiting example, a plurality of subsequences of length k within a larger nucleotide sequence "AGCGUCAUCGUA" may be identified. 3-mers (k=3) may include "AGC," "GCG," "CGU," "GUC," and the like. Apparatus may be configured to iteratively count the number of times each unique K-mer appears within the given sequence. In some cases, computing apparatus may initialize a data structure for K-mer counts storage, for example, and without limitation, a fixed length array having a plurality of indices, each index of the plurality of indices mapped to a unique K-mer, may be used to store the counts.

With continued reference to FIG. 1, in some cases, apparatus may quantify occurrences of K-mers within a set of sequences globally (i.e., across the entire set of sequences). In some cases, set of sequences may include a single long sequence such as a whole RNA genome, or a collection of sequences such as a metagenomic dataset. As a non-limiting example, global K-mer counts may be performed to identify abundance and diversity of microbial species present in a sample by comparing the K-mer profiles to those of known. Additionally, or alternatively, local K-mer counts within specific regions or window 144s of a sequence or across similar regions of multiple sequences may be performed by apparatus. In an embodiment, K-mer patterns in localized area used for identifying sequence motifs associated with biological functions or for studying the variation in K-mer composition across different parts of genome or between different genomic samples may be identified. In cases searching for regulatory elements within IRES regions, local K-mer counts within these specific regions across multiple RNA sequences may be used to reveal common motifs that may indicate a propensity for initiating translation.

With continued reference to FIG. 1, apparatus may generate a feature matrix as a function of both global K-mer counts and local K-mer counts. In an embodiment, feature matrix may include a K-mer count matrix containing both global K-mer counts and local K-mer counts. In some cases, rows of the feature matrix may represent individual sequences or regions in set of sequences, columns of the feature matrix may represent unique K-mers, and each cell in the feature matrix may include the count (or frequency) of the corresponding K-mer in the corresponding sequence. As a non-limiting example, feature matrix may include one or more global features generated by combining global K-mer counts with local K-mer counts. In some cases, apparatus may be configured to eliminate feature counts that don't vary with IRES expression; for instance, and without limitation, K-mers that are commonly presented across all sequences or regions without showing variation in response to different biological states or treatments may be considered less informative and thus excluded from the analysis as described herein.

Continuing to refer to FIG. 1, secondary and/or tertiary structure examples may be represented in an embedding. An "embedding" as used herein, is an element of a vector space. A vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. In some situations, two vectors may be considered equivalent where their directions, and/or the relative quantities of values within each vector as compared to each other, are the same; thus, as a non-limiting example, a vector represented as [5, 10, 15] may be treated as equivalent as a vector represented as [1, 2, 3]. Vectors may be more similar where their directions are more similar, and more different where their directions are more divergent, for instance as measured using cosine similarity as computed using a dot product of two vectors; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute 1 as derived using a Pythagorean norm: $l=\Sigma_{i=0}^{n}a_i^2$, where ai is attribute number i of the vector. Scaling and/or normalization may function to make vector comparison independent of absolute quantities of attributes, while preserving any dependency on similarity of attributes. Two-dimensional subspace of a vector space may be defined by any two orthogonal and/or linearly independent vectors contained within the vector space; similarly, an n-dimensional space may be defined by n vectors that are linearly independent and/or orthogonal contained within a vector space. A vector's "norm" is a scalar value, denoted $\|a\|$ indicating the vector's length or size, and may be defined, as a non-limiting example, according to a Euclidean norm for an n-dimensional vector a as:

$$\|a\| = \sqrt{\sum_{i=0}^{n}a_i^2}$$

Still referring to FIG. 1, embedding may be produced inputting one or more encodings of secondary structures as described above into a model such as a machine-learning model and/or neural network, potentially in combination with corresponding nucleotide sequences, where the machine-learning model and/or neural network is configured to output an embedding encoding secondary and/or tertiary structures and/or representing such structures in vector and/or matrix form; such encoding may combine sequence data and secondary and/or tertiary structures in a single embedding that represents important and/or useful aspects of both. Information about secondary and/or tertiary structures of RNA may be, for instance, recorded as a graph, wherein, for instance, individual nucleotides are encoded as nodes and different types of bonds from such individual nucleotides to other individual nucleotides may be encoded as edge data; as a result, layers of a graph neural network (GNN), for instance as described below, used to generate embeddings may produce node-specific embeddings reflecting and/or representing such relationships. Such embeddings may in turn be converted to an embedding or set of embeddings representing a nucleotide sequence, for example using embedding layers of a GNN as described below.

With continued reference to FIG. 1, assembling training set 112 may include converting each IRES sequence of the plurality of IRES sequences into a corresponding nucleotide sequence data example 116 of the plurality of nucleotide sequence data examples 116 using a representation generation data structure 124. Representation generation data structure 124 may include a neural network, for instance and without limitation as described in further detail below. In a non-limiting example, neural network may include a bidirectional encoder representation from transformer (BERT 128) neural network, for instance and without limitation as described in further detail below.

Further referring to FIG. 1, apparatus 100 may be configured to train representation generation data structure 124. Training may include, without limitation, pretraining stages, training stages, and/or retraining stages. For instance, and without limitation, a BERT 128 or other data structure may be pretrained, trained, and/or validated by apparatus 100 as described below. Alternatively or additionally, a BERT 128 and/or other data structure that has been trained as described below on a first set of training examples may be received and/or instantiated on apparatus 100 and then subjected to additional pretraining, training, and/or validation by apparatus 100 using, for instance, a set of training data containing and/or listing specific categories of nucleotide sequences, such as without limitation IRES sequences, ORNA sequences, or the like. In some embodiments, such a training process may further optimize a model and/or data structure to generate accurate encodings and/or embeddings pertaining to specific categories of nucleotide sequences.

In some embodiments, and still referring to FIG. 1, representation generation data structure 124 may have an input having a first sequence size 132. A "sequence size" as used in this context is a length of sequence that may be input to representation generation data structure 124. For instance, given representation generation data structure 124 may be able to input data representing a fixed number of nucleotides such as for instance 440 nucleotides, where data representing a given nucleotide may include a numerical datum, a vector of numerical data, or the like. In a non-limiting embodiment, a nucleotide sequence and/or Nucleotide sequence 136 of the plurality of nucleotide sequences and/or IRES sequences may have a second sequence size 140 greater than the first sequence size 132; this may render it difficult or impossible for representation generation data structure 124 to generate a representation of such nucleotide sequence and/or Nucleotide sequence 136. In some embodiments, converting Nucleotide sequence 136 to a nucleotide sequence data example 116 of the plurality of nucleotide sequence data examples 116 may include inputting a plurality of sections of the at least one Nucleotide sequence 136, wherein each section has a section sequence size equal to the first sequence size 132, and outputting a plurality of sectional nucleotide sequence data outputs, each one generated by representation generation data structure 124 from the respected section sequence. Apparatus 100 may then aggregate a resulting plurality of sectional nucleotide sequence data outputs and generate the nucleotide sequence data example 116 using the aggregated sectional nucleotide sequence data outputs. Each section sequence may describe at least one nucleotide omitted by each other section sequence; this may be accomplished, without limitation, using a "window" 144 having the first sequence size 132 that begins at one end of nucleotide and/or Nucleotide sequence 136, with a first edge of the window 144 at the end of the sequence and the second end a number of nucleotides from the first end that is equal to the first sequence size 132, such that the first sectional input is a sequential list of nucleotides of the nucleotide and/or Nucleotide sequence 136 running from the one at the selected end to the one the first sequence size 132 from it. Each subsequent section sequence may be generated by moving the first edge of the window 144 one or more nucleotides away from the selected end, while keeping the width of the window 144 fixed, so that, for example when the window 144 has been shifted by n nucleotides, the section sequence runs from the 1+nth nucleotide to the first section 148 size+nth nucleotide. This may be repeated until all nucleotides have been input at least once, or until the first edge of the window 144 reaches the opposite end of the sequence.

Still referring to FIG. 1, apparatus 100 may aggregate sectional outputs. In some embodiments, sectional outputs may be averaged together, for instance by computing an element-wise arithmetic, geometric, or other mean of vector elements output for each sectional output. Alternatively or additionally, aggregation may include inputting all sectional inputs to a data structure such as a neural network, machine-learning model, or the like that is trained to generate an aggregated embedding using, e.g., pooling, convolutional, and/or decimating layers. Such an aggregation model may be tuned by evaluating, e.g., phylogenetic clustering and/or evaluations used to generate error functions and/or tuning for a BERT 128 as described in further detail below; tuning may be performed iteratively until aggregated embeddings converge to within a threshold value of criteria to which they are compared.

With continued reference to FIG. 1, in some embodiments apparatus 100 may be configured to determine one or more tests or metrics of quality, performance, and/or efficacy with regard to embeddings and/or other representations of a nucleotide sequence to be used as nucleotide sequence data example 116; such metrics, as used in this disclosure, may be referred to as "efficacy metrics." Test or metrics may be used, e.g., to trigger further retraining of representation generation data structure 124, to indicate to a user of apparatus 100 that one or more outputs of representation generation data structure 124 are insufficient for use in subsequent method steps, or the like. In either case, test output and/or metric may be compared to a threshold value, acceptable range of values, epsilon neighborhood, or other measure of convergence or quality; such comparison may include subtraction or other calculations to generate an error and/or error function, which may be used for retraining, and/or to generate a flag or alert to inform a user. Alternatively or additionally, multiple representation generation data structure 124 candidates may be generated, instantiated, pretrained, and/or retrained followed by comparison of each to one or more metrics and/or tests; a candidate that outperforms other candidates per such comparison may be selected for use generally or with respect to a particular input with regard to which apparatus 100 may be determining an activity and/or probability of activity using elements and/or methods described herein.

Still referring to FIG. 1, metric or test may include a determination of a degree to which embeddings produced by representation generation data structure 124 and/or a representation generation data structure 124 candidate cluster by phylogeny, or in other words whether representations of nucleotide sequences, when clustered according to a measure of geometric similarity or other clustering criterion, are also clustered together according to a biological species of origin, for instance and without limitation as described in further detail below. Alternatively or additionally, metric and/or test may include determining whether representations of nucleotide sequences cluster, under a selected clustering process, according to other criteria of similarity between nucleotide sequences, biological origins thereof, or the like.

Continuing to refer to FIG. 1, apparatus 100 is configured to partition training set 112 into at least a first section 148 and a second section 152. First section 148 may be used for pretraining or first stages of training as described below, while second section 152 may be used for a later training stage and/or retraining. In some embodiments, apparatus 100 may be configured to partition training set 112 into a first section 148, a second section 152, and a third section 156, where the first section 148 is used to for pretraining and/or a first round of training, the second section 152 is used for training, retraining, and/or a second round of training and/or validation, and the third section 156 is used as a holdout and/or testing section, for instance and without limitation as described in further detail below. In some embodiments, first section 148 may have a first size and/or number of training examples, and second section 152 may have a second size and/or number of training examples. First size and/or number of training examples may be greater than second size and/or number of training examples; for instance, and without limitation, first size may be approximately 80% of training examples in training set 112, while second size may be approximately 20% of training examples in training set 112. Second size and/or number of training examples may exceed and/or equal first size and/or number of training examples in some embodiments. Where partitioning includes partitioning into a first section 148, a second section 152, and a third section 156, the sections may have respectively a first size and/or number of training examples, a second size and/or number of training examples, and a third size and/or number of training examples. First, second, and third size and/or number of training examples may be equal, or any one of the three may be greater and/or smaller than any other of the three, in some embodiments. For instance, and without limitation, first size and/or number of examples may be larger than either second size and/or number of examples; as a non-limiting example, first size and/or number of training examples may be approximately 80% of the total number of training examples in training set 112, while second size and/or number of training examples and third size and/or number of training examples may combine to make up the other approximately 20%, for instance and without limitation being approximately 10% each. Persons skilled in the art, upon reviewing the entirety of this disclosure, will be aware of various proportions that may be used in two, three, or more section partitions.

Further referring to FIG. 1, each partition into two, three or more sections may be selected to reflect or maintain one or more statistical properties of training set 112 as a whole. For instance, each of a first section 148, second section 152, and/or third section 156 in a partition may have a proportion of highly active, moderately active, and/or less active IRES or other sequences that may equal or match approximately a proportion of highly active, moderately active, and/or less active IRES or other sequences in training set 112 as a whole; where activity and/or probability of activity is represented continuously or quasi-continuously, such as where activity and/or probability of activity is a value along a continuum running from inactive to highly active with intermediate values therebetween representing increasing activity, training set 112 may have a probability distribution function (pdf), having an x-axis representing activity and a y-axis representing probability of presence within activity set indicating relative probability of presence of an activity and/or probability of activity at each point along the continuum, where a given activity's, and/or probability of activity's, probability may be found or approximated by integration of the pdf proximate to the activity and/or probability of activity or the like; each section of a partition may likewise have a pdf representing probability of continuously represented activity and/or probability of activity, where each section's pdf is equivalent to or closely matches the pdf of the activity set. As a further example, training set 112 may include representations and/or examples of sequences having more than one biological origin, such as sequences having origins in various species and/or genera of living organism, viruses, or the like; training set 112 may have a relative distribution of biological origins for sequences represented therein, such as a first proportion of sequences having a first biological origin (e.g. a first species and/or genus of origin), a second proportion of sequences having a second biological origin (e.g. a second species and/or genus of oration), and/or a plurality of proportions corresponding to a plurality of biological origins. Each section of a partition may be selected to have a similar or the same proportion of sequences by biological origin as in training set 112 as a whole. In an embodiment, each partition may be selected to match each of two or more distributions represented in training set 112; for instance, each section of a partition may have the same or similar distribution of activity as training set 112, while also having the same or similar distribution of biological origins as training set 112.

With continued reference to FIG. 1, apparatus 100 may be configured in some embodiments to divide multiple copies of training set 112 into multiple partitions 160*a*-*n* of two, three, or more sections. Multiple partitions may be mutually distinct; in other words each first, second and/or third section 156 may have at least some training examples not found in the respective first, second and/or third sections 148 of other partitions. First section, second section, and/or third section may be mutually disjoint. Apparatus 100 may perform each partition to have relative sizes and/or numbers of training examples per section as described above; in some embodiments, each partition may have the same or similar sizes for its first, second, and/or third section 156 as compared to each other partition. Apparatus 100 may be further configured to select each partition of a plurality of partitions to have statistical properties of training set 112, such as distribution of activity and/or biological origin as described above. In an embodiment, apparatus 100 may use plurality of partitions may be used to train a plurality of candidate data structures, models, and/or neural networks as described in further detail below.

Still referring to FIG. 1, apparatus 100 is configured to train, using first section 148, at least an activity data structure 164*a*-*m* to generate probable IRES activity 120 and/or other activity using nucleotide sequence data. Probable IRES and/or other activity may be represented in any suitable manner. For instance, and without limitation, an IRES or other activity may be represented as a numerical value or score, such as a numerical value or score placed on a continuum from a lower numerical value or score representing no or essentially no activity to an upper numerical value or score representing a maximal IRES or other activity; in some embodiments continuum may have no upper and/or no lower value, such as a number line running from 0 to an indefinitely high number and/or infinity. Alternatively or additionally, an IRES or other activity may be represented as one of two or more discrete values such as Boolean variables, state variables, linguistic variables or the like, such as classification to logic 0 or "not active" and logic 1 or "highly active", classification to "not active," "moderately active," and "highly active," or the like. Outputs may be defined, without limitation, using ranges on a continuum and/or fuzzy sets as described in further detail below. Various output types may be derived from or interchanged with other output types. As a non-limiting example, discrete values may represent membership in ranges on a continuum; for instance, an output of activity data structure 164*a*-*m* may include a numerical value such as an integer or floating point value representing a score and/or placement on a continuum as described above, which may be compared to one or more thresholds and/or divisions between ranges to produce a discrete value. Alternatively or additionally, activity data structure 164*a*-*m* may have an output such as a binary encoding, which may include, without limitation, one-hot encoding, Gray encoding, or the like which may directly represent discrete classifications. Persons skilled in the art, upon reviewing the entirety of this disclosure, will be aware of various ways in which activity may be represented consistently with this disclosure. Activity and/or probabilities may be grouped into two classes, n classes for some number n, indicating a probability of a sequence being in any activity bucket, set, and/or fuzzy set, such as for example, low-mid-high, and/or showing an actual activity number, represented for instance using a reading from a point on a continuum represented by a given output, a TSK or other defuzzification output as described in further detail below, or the like; for example an actual activity number may include an actual expressed luminescence value produced using a physical sample wherein a given IRES is attached to a gene that upon production produces luminescence, phosphorescence, or the like, such as without limitation luciferase in the presence of luciferin. Activity in training set 112 may be encoded and/or represented in an equivalent manner to those output by activity data structure 164*a*-*m*; alternatively, output of activity data structure 164*a*-*m* and/or activity in training data may be converted to matching forms for input to error functions or the like. Similarly, activity may be transformed into one or more display elements such as a graphical depiction of a continuum, a numerical representation of a score, a word and/or color representing a discrete value or placement in a range, or the like; such display elements may be displayed to a user of apparatus 100 in a graphical user interface.

Continuing to refer to FIG. 1, at least an activity data structure 164*a*-*m* may include one or more machine-learning models, neural networks, and/or combinations thereof in one or more sections or stages. For instance, and without limitation, at least an activity data structure 164*a*-*m* may include at least an activity neural network. At least an activity neural network may include a graph neural network, for instance and without limitation as described in further detail below. In an embodiment, information about secondary and/or tertiary structures of RNA May be, for instance, recorded as a graph, wherein, for instance, individual nucleotides are encoded as nodes and different types of bonds from such individual nucleotides to other individual nucleotides may be encoded as edge data; as a result, layers of a graph neural network (GNN) used to generate embeddings may produce node-specific embeddings reflecting and/or representing such relationships; these in turn may be analyzed using later stages of a GNN to, e.g., identify structures that are of greater importance to IRES or other activity. In some embodiments, such identification may be used in a final neural net or other data structure stage to classify IRES sequences to activity and/or to calculate scores representing activity. At least an activity neural network may include a convolutional neural network, for instance and without limitation as described in further detail below. At least an activity neural network may include a deep neural network, for instance and without limitation as described in further detail below. Generally, at least an activity neural network may include any suitable combination of feed-forward, feedback, pooling, decimating, interpolating, convolutional, or other stages and/or layers as described in this disclosure.

As a non-limiting example, and still referring to FIG. 1, activity data structure 164a-m may include a network, which may include without limitation a feed-forward deep learning network, having a one or more decimation and/or pooling stages that reduce a number of input elements down to a smaller output such as an encoding of a classification to discrete values and/or a numerical value of score representing a degree of activity and/or placement on a continuum, as described above. For instance, and without limitation, a representation of a nucleotide sequence as generated by representation generation data structure 124 may include a plurality of embeddings and/or other data structures corresponding to each nucleotide in sequence and explicitly and/or implicitly representing, without limitation, structural, pairing, adjacency or other values pertaining to the nucleotide and its relationships to other nucleotides and/or other portions of the sequence, or aggregations of such representations using sequence sections, window 144ing, and/or aggregation as described above. As a non-limiting illustration, where a sequence size of representation generation data structure 124 is 440, pertaining to a sequence and/or sequence window 144 corresponding to 440 nucleotides, and each of 440 outputs includes an embedding with 120 elements, activity data structure 164a-m may have 52,800 input nodes corresponding to a 440/120 and may reduce node counts and/or layer outputs by stages and/or layers to 2048 nodes, then 256 nodes, then 2 nodes to represent a binary encoding, for instance where output is potentially binary (0 or 1), or 1-hot with 10 representing active, 01 representing inactive, or using 00 as fully inactive, 11 as "active," and intermediate values representing medium intermediate degrees of activity; reduction may, in a similar example be to a number of bits used to represent a numerical value on a continuum using an "int" floating-point, double precision, or other mathematical representation, which may be unsigned, 2s-complement, or any other suitable form.

Continuing to refer to FIG. 1, in some embodiments, and without limitation, input to activity data structure 164a-m may be sequences, structural encodings, or the like that have not been processed by a representation generation data structure 124. For instance, activity data structure 164a-m may include a 1-step machine-learning model, neural network, or the like, which may combine sequence and structural details regarding each nucleotide sequence to determine activity. As a non-limiting example, where structural elements are encoded and/or represented as a graph or as graph embeddings pertaining to each nucleotide, such embeddings may be generated by and/or input to a GNN, for instance and without limitation as described below, which may be pretrained trained, validated, or the like to generate activity as described above. As a further non-limiting example, embeddings representing dot-bracket notation of structural features, outputs of embedding generation stages of a GNN, and/or values representing Shannon entropy may be input for each element in a sequence to a CNN, which may be pretrained, trained, and/or validated therewith to generate activity as described in further detail below.

Still referring to FIG. 1, training activity data structure 164a-m on first section 148 may include, without limitation, a pretraining process. Pretraining may include, without limitation, any pretraining as described in this disclosure. Pretraining may include, without limitation unsupervised learning processes, which may, for instance identify correlations between nucleotide sequence data example 116 features and/or attributes and activity, the latter of which are output owing to the structure of the activity data structure 164a-m. Alternatively or additionally, pretraining and/or training on first section 148 may include supervised learning, wherein outputs may be compared to activity corresponding to nucleotide sequence data examples 116 in first section 148, generation of an error function, and adjustment of weights and/or biases as described in further detail below. Training and/or pretraining using first section 148 may proceed until all errors produced by an error function and/or any aggregation thereof is within a preconfigured convergence threshold, epsilon value and/or neighborhood, or the like.

With continued reference to FIG. 1, apparatus 100 is configured to iteratively retrain at least an activity data structure 164a-m using the second section 152. In some embodiments use of second section 152 in retraining may include and/or signify use of second section 152 in an evaluation process to trigger retraining using examples from first section 148 and/or second section 152. In other words, second section 152 may be used to evaluate whether further retraining using examples from second section 152 and/or examples from first section 148 is to be performed. For instance, at least an exemplary nucleotide sequence data example from second section may be input to at least an activity data structure, which may output at least a predicted IRES activity value to be compared to at least an IRES activity value from the at least an example from second section—at least a predicted IRES activity value and at least an IRES activity value from the at least an example from the second section may be compared using any error function below. A plurality of examples from second section may be used, and one or more error function and/or other comparison results evaluated to determine if additional training and/or retraining is to be performed. Evaluation of error function and/or other comparison results may include comparison of each of error function and/or other comparison results to a maximum single error threshold; in other words, a criterion of evaluation may include performing iterative retraining if any single comparison and/or error function output exceeds maximum single error threshold or if a count of single comparison and/or error function outputs exceeding single error threshold exceeds a threshold number and/or proportion of overall error function and/or other comparison results. Alternatively or additionally, evaluation of error function and/or other comparison results may include comparison of an aggregated plurality of error function and/or other comparison results to an aggregate error threshold; in other words, a criterion of evaluation may include performing iterative retraining if a result of averaging or otherwise aggregating a plurality such as some or all evaluated function and/or other comparison results exceeds aggregate error threshold. Aggregation may be performed in any manner of aggregation described in this disclosure and/or any combination thereof. Criteria for evaluations may be evaluated separately such that failing any one criterion causes iterative retraining; alternatively or additionally evaluation results may be combined according to one or more logical or other rules.

Iterative retraining, once triggered by, e.g. evaluation using second section 152, may include generating a predicted IRES activity value using the at least an activity neural network and a nucleotide sequence data example 116. Example 116 may be taken from second section 152 and/or may be taken from first section 148 as part of a retraining process triggered by evaluation of a training example of second section 152. Iterative retraining includes evaluating an error function using predicted IRES activity value and an observed IRES activity 120 correlated to nucleotide sequence data example 116. Error function may, in a non-limiting example, involve comparison of an output of activity data structure 164a-m to a corresponding activity in second section 152. For instance, where output and activity are numerical scores, error function may include subtraction of one from the other to derive an absolute value and/or mean squared error. Where output and/or activity in training set 112 is represented as a binary classification, an error function may include a hinge loss function, sigmoid cross entropy loss function, weighted cross entropy loss function, or the like. Where output and/or activity in training set 112 is a classification to three or more values, error function may include a softmax cross entropy loss function, a sparse cross entropy loss function, a Kullback-Leibler divergence loss function, or the like. Iterative retraining includes tuning at least an activity data structure 164a-m using evaluated error function. Use of error functions and/or training processes may be performed in any manner consistent with this disclosure. Where both retaining and training with first section 148 include supervised training, retraining may use a different error function, different weight update functions and/or parameters, or the like than in the training stage. For instance, and without limitation, when a previous iterative retraining process included training using examples from first section 148 and/or second section 152 until a first convergence threshold and/or epsilon value and/or neighborhood is met, a subsequent iterative retraining process may include a lower convergence threshold, a smaller value of epsilon, or the like. Iterative retraining may include using one or more examples from first section 148 and/or second section 152 that were not used in any previous training and/or retraining process; for instance, where convergence was initially and/or previously achieved using a first subset of examples from first section 148, a subsequent retraining process may use examples from a second subset of first section 148 which may be wholly disjoint from first subset and/or have one or more elements that are not found in first subset.

With continued reference to FIG. 1, where partition of training set 112 includes a third section 156, such as a holdout section, apparatus 100 may use third section 156 to evaluate and/or test output of trained activity data structure 164a-m. For instance, and without limitation, apparatus 100 may input nucleotide sequence data examples 116 into trained activity data structure 164a-m and compare outputs to corresponding activity in training set 112. Comparison may include, without limitation, identification and enumeration of correct and incorrect classifications, subtraction of score and/or other numerical values to determine an amount of raw error, and/or calculation of any error function as described herein; comparison may further include aggregation of results, such as determination of an error rate in classification, an average value of raw subtractive error, squared or absolute value error, and/or of error function, which may be compared to a threshold and/or convergence parameter. In some embodiments, where aggregate value representing error fails a convergence and/or threshold test, apparatus 100 may repeat one or more training, pretraining, and/or retraining steps, for instance and without limitation with an additional partition of training set 112, or by producing and utilizing a new training set 112.

Further referring to FIG. 1, and by way of illustration, training examples may be split into to three sections making up a first section 148 for training, a second section 152 for validation, and a third section 156 for testing. At least an activity data structure 164a-m may be trained using only the training set and corresponding activity and/or probabilities; in this step at least an activity data structure 164a-m may be trained to find, and/or embody a data structure representing, a mathematical function between sequence representations and corresponding activity and/or probabilities for each sequence in the training set. Continuing the above-described example, apparatus may then test trained at least an activity data structure 164a-m on validation set to determine how accurately at least an activity data structure 164a-m can predict activity and/or probabilities on a set of new sequence from validation set. One or more parameters of at least an activity data structure 164a-m may be modified and/or reset prior to retraining. For instance, and without limitation, one or more biases, weights, activation function coefficients, or the like of at least an activity data structure 164a-m may be changed and/or replaced by a random amount within some numerical range; all parameters may be so modified and/or a subset may be modified, for instance by selection using a random number function, a pseudorandom number function, or the like. At least an activity data structure 164a-m may then be retrained, potentially from scratch, on training set; after convergence, apparatus 100 may then test the retrained and/or new model on validation set again. This cycle may be repeated many times until at least an activity data structure 164a-m with best performance and/or performance within thresholds as described above on validation set is produced. Apparatus 100 may then test at least an activity data structure 164a-m so trained on the third section 156 and/or testing set, to see how generalizable at least an activity data structure 164a-m is for predicting the activity of completely new sequences; this testing may include use of other maximum and/or aggregate error thresholds, wherein failure of threshold tests may trigger additional retraining cycles and/or repetition of one or more steps as described above.

Alternatively or additionally, and still referring to FIG. 1, apparatus 100 may be configured to use a plurality of partitions, as described above, to train a plurality of activity data structure 164a-m candidates. Each activity data structure 164a-m candidate may have the same structure and training process, albeit with different partitions of training set 112; alternatively, each activity data structure 164a-m may have a different structure, different initial weights, update function parameters, different pretraining and/or tuning processes, and/or different error functions than each other activity data structure 164a-m. In some embodiments, update parameters, learning rate parameters, and/or error function coefficients and/or weights may be selected randomly and/or pseudo-randomly on a range of potentially acceptable values. In some embodiments, test results may be compared according to one or more metrics of efficacy, such as reliability, which may represent a fraction of active IRES and/or sequences in predicted active IRES and/or sequences and/or hit rate, which may represent a fraction of correctly predicted active IRES and/or sequences in a section of training set 112 used for evaluation. In some embodiments, and without limitation, apparatus 100 may be configured to select for use an activity data structure 164a-m of plurality of activity data structure 164a-m candidates that has a highest or best score according to one metric of efficacy, such as a highest or best reliability score, a highest or best hit rate, or the like. Alternatively or additionally, apparatus 100 may be configured to select for use an activity data structure 164a-m of plurality of activity data structure 164a-m candidates that has a highest or best aggregate score, such as an aggregation of hit rate and reliability according to a weighted average or other aggregation. Alternatively or additionally, apparatus 100 may be configured to select for use an activity data structure 164a-m of plurality of activity data structure 164a-m candidates that has a greatest degree of convergence during training, retraining, or the like. Persons skilled in the art, upon reviewing the entirety of this disclosure, will be aware of various ways in which a candidate activity data structure 164a-m may be selected for use.

Still referring to FIG. 1, in some exemplary embodiments, apparatus 100 may be configured to receive and/or input to at least an activity data structure 164a-m an IRES sequence 168 and/or other nucleotide sequence, such as without limitation a sequence believed or suspected to be an IRES sequence 168 or capable of translation thereto and output a probable IRES activity 172 using the at least an activity data structure 164a-m. Nucleotide sequence and/or data describing nucleotide sequence, may be input to activity data structure 164a-m in any form and/or after any processing, encoding, and/or embedding steps, as described above. Activity 172 may be displayed to a user, for instance using a graphical user interface as noted above. Alternatively or additionally, one or more automated processes using a given input sequence may be triggered by determination that a sequence has a high probable activity, such as for instance initiation of an experimental process to confirm activity, evaluate therapeutic effects of IRES sequence 168 such as an ORNA containing IRES in question, or the like. Results of experimental evaluation of activity of sequences may be compared to predicted activity, for instance to generate a new error function for further tuning, create new training data for tuning or any other training or testing process described above, and/or to detect that activity data structure 164a-m is not performing as well as desired; in the latter case, activity data structure 164a-m may be retrained further and/or apparatus 100 may repeat one or more steps as described above to generate a new instance of an activity data structure 164a-m.

Further referring to FIG. 1, it should be noted that each pre-training, retraining, and/or retraining with more specific datasets such as without limitation IRES datasets may be performed by apparatus 100 and/or by one or more remote devices; apparatus 100 may instantiate generation data structure at apparatus 100 after any or all training stages, and/or may retrain further upon instantiation.

Figure 2:
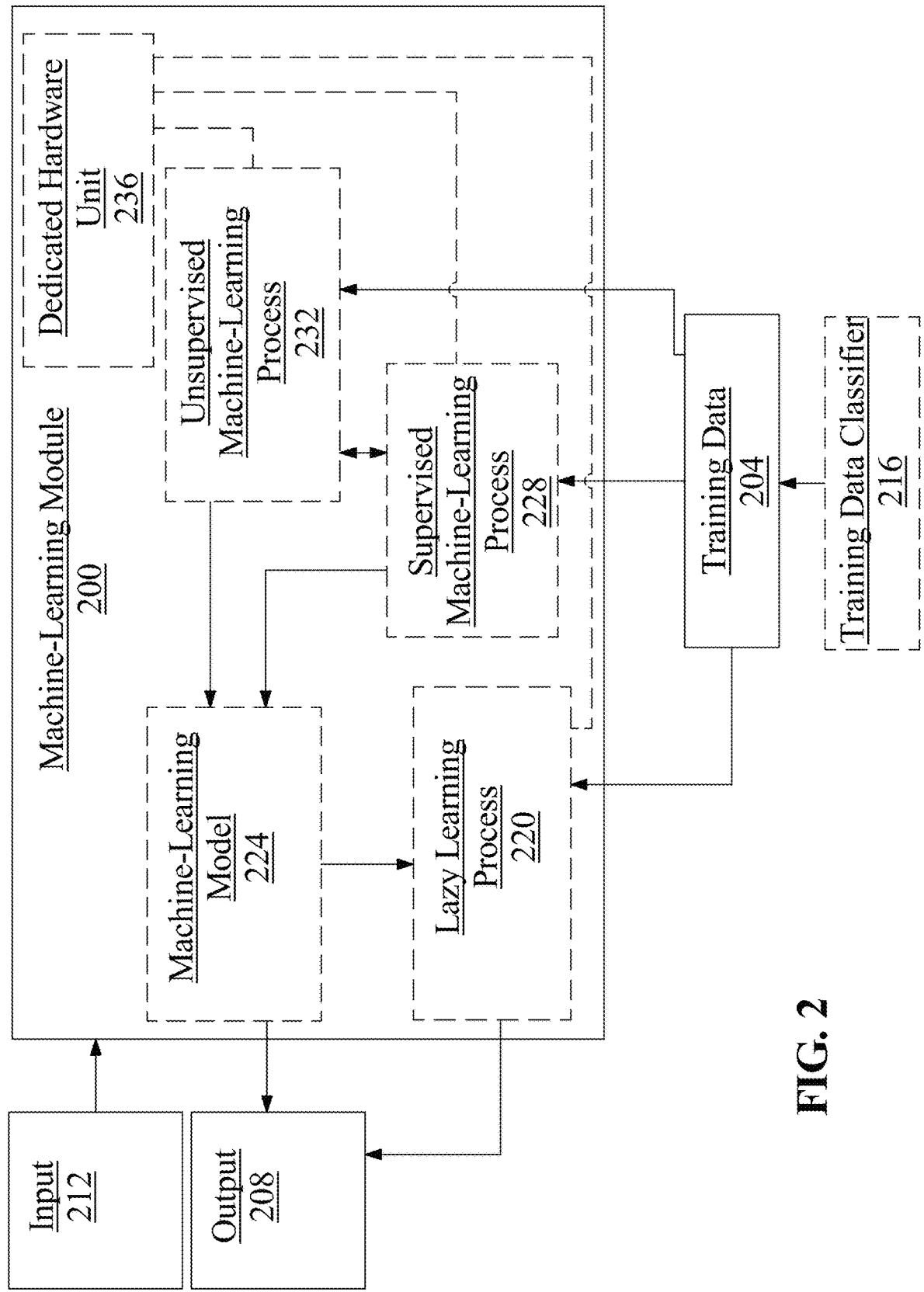
FIG. 2 is a block diagram illustrating an exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data according to one or more attributes that may, for instance, be useful in improved distributions across partitions.

Still referring to FIG. 2, computing device 204 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)=P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 204 may then calculate a likelihood table by calculating probabilities of different data entries and classification labels. Computing device 204 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, computing device 204 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: $l=\Sigma_{i=0}^{n}a_i^2$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 2, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 2, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 2, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 2, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

With continued reference to FIG. 2, a machine learning module as described herein, may implement a gradient boosting framework. In one or more embodiments, machine learning module may be configured to build models in a stage-wise fashion, for example, and without limitation, machine learning module may construct one or more new models that correct the errors made by previously trained models and combines them to produce final predictions such as predictions of IRES and/or nucleotide activity may include one or more XGBoost models that specifically optimize gradient boosting algorithm for speed and performance. In some cases, activity prediction model may incorporate one or more regularization terms (L1 and L2 regularization) in its objective function to prevent overfitting. In some cases, models such as for instance activity prediction model may be configured to handle sparse data, originating from missing values or zero entries, through a sparsity-ware algorithm; for instance, and without limitation, this may involve selectively focusing on non-zero K-mer counts within feature matrix as described above to predict gene expression levels. In some cases, activity prediction data structure may be configured to run on a single machine as well as on distributed computing environments such as, without limitation, HADOOP, SPART, DASK, and/or the like. In one or more embodiments, activity prediction data structure may support various objective functions and evaluation criteria, for example, and without limitation, one or more objective functions may include minimizing the difference between predicted and actual expression levels, while evaluation criteria may focus on accuracy, precision, recall, or area under the ROC curve (AUC) to assess model performance. In an embodiment, XGBoost's model training may involve minimizing an objective function that consists of a loss term and a regularization term. For a given dataset with n instances and m features, objective function at iteration t may be expressed as:

$$Obj^t = \sum_{i=1}^{n} l(y_i, \hat{y}^{t-1} + f_t(x_i)) + \Omega(f_t)$$

Where $y_i$ is the true label for instance i, $\hat{y}^{t-1}$ is the predicted label for instance i at iteration t−1, $f_t$ is the model (i.e., decision tree) added at iteration t, l is a differentiable convex loss function that measures the difference between the predicted label and the true label, and $\Omega$ represents the regularization term which penalizes the complexity of the model to avoid overfitting. As a non-limiting example, activity prediction model may include a random forest in which XGBoost may be implemented to utilize a depth-first approach and prune trees using a max_depth parameter. Activity prediction data structure may dynamically split up to the specific max_depth and then start pruning the tree backwards, removing splits that do not contribute to a positive gain in predictive accuracy. At each iteration of the boosting process, activity prediction data structure may perform a cross-validation on the dataset.

Figure 3:
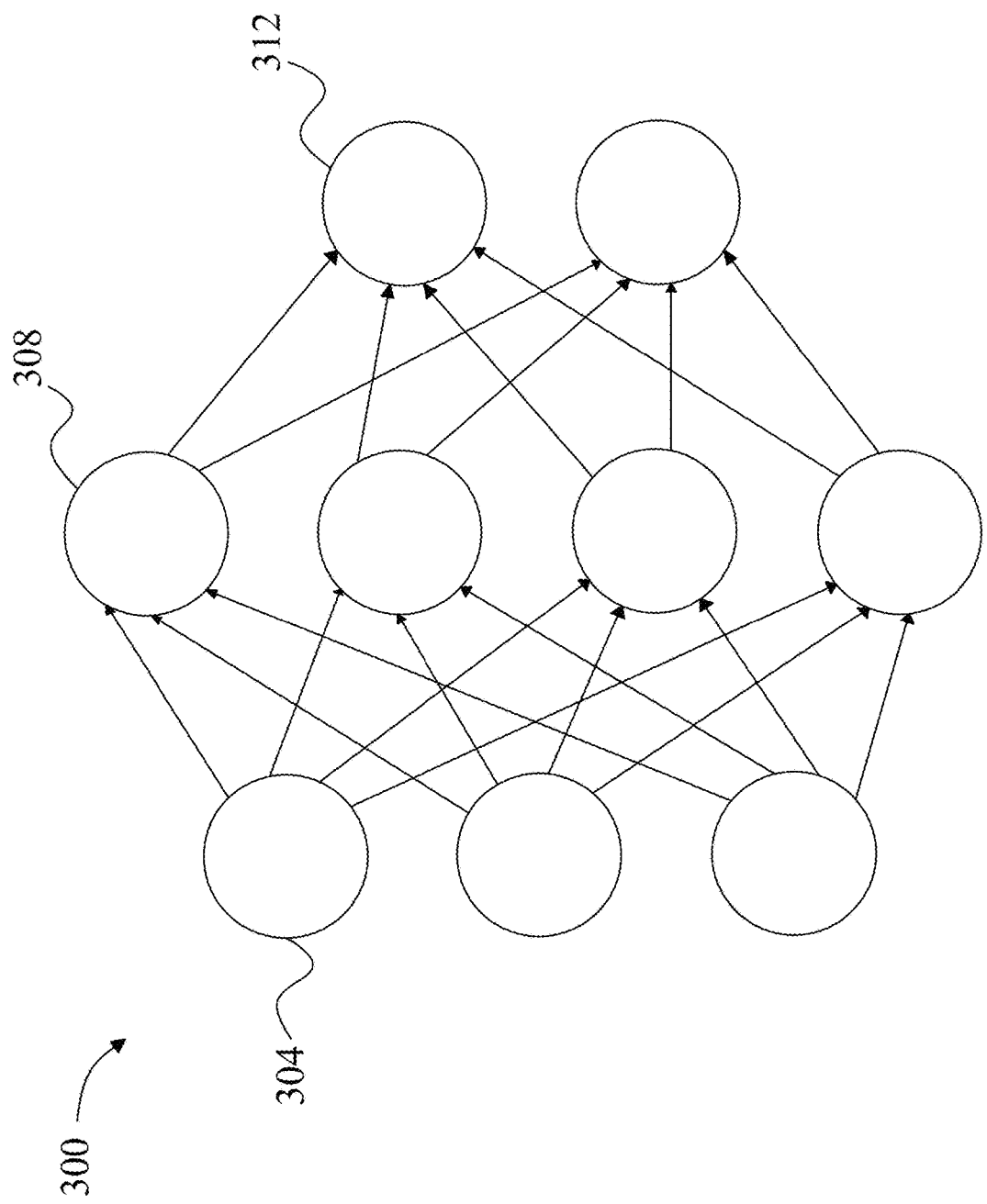
FIG. 3 is a schematic diagram illustrating an exemplary embodiment of a neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
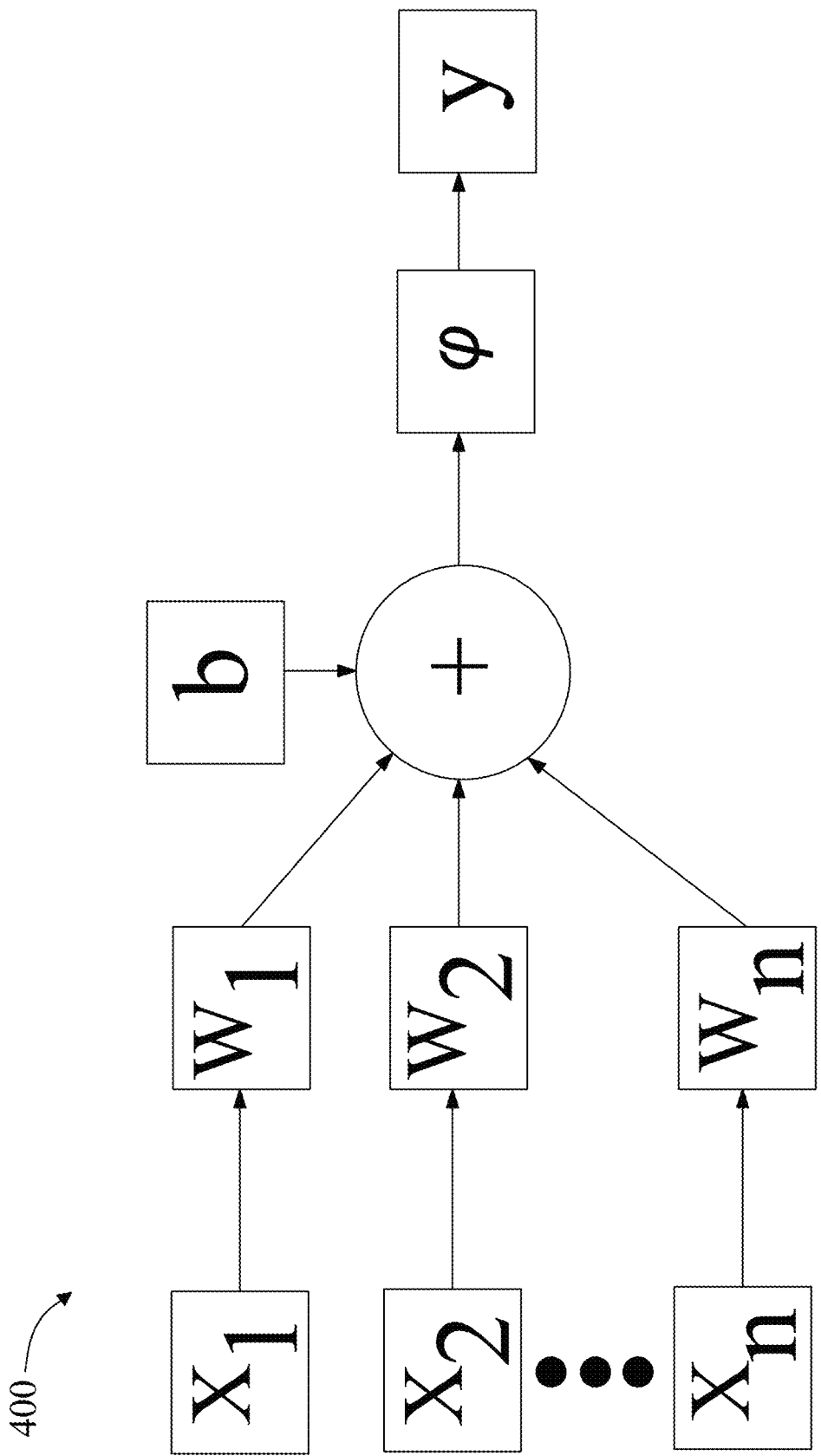
FIG. 4 is a schematic diagram illustrating an exemplary embodiment of a node of a neural network.

Referring now to FIG. 4, an exemplary embodiment of a node 400 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tan h (hyperbolic tangent) function, of the form $$\frac{e^x - e^{-x}}{e^x + e^{-x}},$$

a tan h derivative function such as $f(x) = \tanh^2(x)$, a rectified linear unit function such as $f(x) = \max(0, x)$, a "leaky" and/or "parametric" rectified linear unit function such as $f(x) = \max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x) = x * \text{sigmoid}(x)$, a Gaussian error linear unit function such as $f(x) = a(1 + \tan h(\sqrt{2/\pi}(x + bx^r)))$ for some values of a, b, and r, and/or a scaled exponential linear unit function such as $$f(x) = \begin{cases} \alpha(e^x - 1) & \text{for } x < 0 \\ x & \text{for } x \geq 0 \end{cases}.$$

Fundamentally, there is no limit to the nature of functions of inputs x; that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above. Each weight in a neural network may, without limitation, be updated and/or tuned, based on an error function J, using a backpropagation updating method, such as:

$$w_{new} = w_{old} - \alpha \frac{dJ}{dw}$$

where $w_{new}$ is the updated weight value, Wold is the previous weight value, a is a parameter to set the learning rate, and $$\frac{dJ}{dw}$$

is the partial derivative of with respect to weight w.

With continued reference to FIG. 4, in an embodiment, a neural network may include a deep neural network (DNN). As used in this disclosure, a "deep neural network" is defined as a neural network with two or more hidden layers. In a non-limiting example, a neural network may include a convolutional neural network (CNN). Training activity data structure and/or representation generation data structure may include training a CNN using above-described training sets and predicting IRES and/or sequence activity, and/or generating representations of sequences, using trained CNN. A "convolutional neural network," for the purpose of this disclosure, is a neural network in which at least one hidden layer is a convolutional layer that convolves inputs to that layer with a subset of inputs known as a "kernel," along with one or more additional layers such as pooling layers, fully connected layers, and the like. In some cases, CNN may include, without limitation, a deep neural network (DNN) extension. Mathematical (or convolution) operations performed in the convolutional layer may include convolution of two or more functions, where the kernel may be applied to input data through a sliding window 144 approach. Additionally, or alternatively, CNN may also include one or more pooling layers, wherein each pooling layer is configured to reduce the dimensionality of input data while preserving essential features within the input data. In a non-limiting example, CNN may include one or more pooling layer configured to reduce the spatial dimensions of spatial feature maps by applying downsampling, such as max-pooling or average pooling, to small, non-overlapping regions of one or more features.

Still referring to FIG. 4, CNN may further include one or more fully connected layers configured to combine features extracted by the convolutional and pooling layers as described above. In some cases, one or more fully connected layers may allow for higher-level pattern recognition. In a non-limiting example, one or more fully connected layers may connect every neuron (i.e., node) in its input to every neuron in its output, functioning as a traditional feedforward neural network layer. In some cases, one or more fully connected layers may be used at the end of CNN to perform high-level reasoning and produce the final output such as, without limitation, IRES and/or sequence activity and/or embeddings and/or representations of RNA sequences. Further, each fully connected layer may be followed by one or more dropout layers configured to prevent overfitting, and one or more normalization layers to stabilize the learning process described herein.

With continued reference to FIG. 4, in an embodiment, training CNN may include selecting a suitable loss function to guide the training process. In a non-limiting example, a loss function that measures the difference between the predicted representation and/or activity and experimentally derived activity and/or an expected representation may be used, such as, without limitation, mean squared error (MSE) other loss functions described in this disclosure, or a custom loss function may be designed for one or more embodiments described herein. Additionally, or alternatively, optimization algorithms, such as stochastic gradient descent (SGD), may then be used to adjust the CNN parameters to minimize such loss. Additionally, CNN may be extended with additional deep learning techniques, such as recurrent neural networks (RNNs) or attention mechanism, to capture additional features and/or data relationships within input data.

With continued reference to FIG. 4, apparatus 100 may be configured to generate representations and/or embeddings based on nucleotide sequences using a Bidirectional Encoder Representations from Transformers (BERT). In an embodiment, BERT may implement a transformer architecture having an "attention mechanism" configured to dynamically determine and assign weight e.g., importance of different tokens such as text characters, words, nucleotides, kmers, or the like. Exemplary attention mechanism may include, without limitation, generalized attention self-attention, multi-head attention, additive attention, global attention, and the like. In some cases, transformer architecture may be implemented as an encoder-decoder structure having an encoder configured to map an input sequence to a higher dimensional space i.e., a sequence of continuous representations, and a decoder configured to transform output of the encoder into a final output sequence, such as without limitation an embedding representing a nucleotide sequence. In other cases, transformer architecture may include only an encoder stack. As a non-limiting example, BERT may include a plurality of layers each contains one or more sub-layers, wherein a first sub-layer may include a multi-head self-attention mechanism, and a second sub-layer may include a position-wise fully connected feed-forward network. In some cases, plurality of layers may be identical. In some cases, multi-head self-attention mechanism may configure BERT to focus on different parts of the input sequence when predicting elements of an embedding to be output; for instance, and without limitation, self-attention mechanism may be described by an attention function:

$$\text{Attention}(Q, K, V) = \text{softmax}\left(\frac{QK^T}{\sqrt{d_k}}\right)V$$

Where Q, K, and V represent a set of queries, keys, and values matrices respectively, and $d_k$ is the dimensionality of the keys. In a non-limiting embodiment, in the context of analysis of RNA, a self-attention mechanism may take output of previous layer X and produce outputs C, using weight matrices $W_i^V$ based on query matrix $Q_i=[q_1^i, \ldots, q_n^i]$, key matrix $K_i=[k_1^i, \ldots, k_n^i]$, and value matrix $V_i=[v_1^i, \ldots, v_n^i]$ as follows:

C=Concat (head$_1$, . . . , head$_H$)W$^0$ (inner product with the W one)

$$\text{head}_i = \text{softmax}\left(\frac{(Q_i)(K_i)^T}{\sqrt{D}}\right)V_i$$

where $Q_i=XW_i^Q, K_i=XW_i^K, V_i=XW_i^V$ representing inner products with sets of weights $W_i^Q$, $W_i^K$, and $W_i^V$, which are the weights to be tuned when training BERT. These matrices may be of size D×D that where D is the input and output vector dimension, which may be, as a non-limiting example, 120 elements. In the above-described example, each head may calculate a subsequent hidden state by computing an attention-weighted sum of a value vector v.

In some cases, and still referring to FIG. 4, position-wise fully connected feed-forward network within second sub-layer of each layer may apply a linear transformation to each position separately and identically, for example, and without limitation, position-wise fully connected feed-forward network may be configured to process the output of the attention mechanism according to equation FFN(x)=max (0, xW$_1$+b$_1$) W$_2$+b$_2$, where W$_1$, W$_2$, b$_1$, and b$_2$ are parameters of the feed-forward and x is the input to the feed-forward network. In other words, second sub-layer may include two convolutions with a kernel size 1 and a ReLu activation in between.

With continued reference to FIG. 4, in one or more embodiments, BERT's input representation may combine a plurality of embeddings of tokens, segments, and/or positions. In some cases, each token may be processed, for example and without limitation, through a WordPiece tokenization. Output of BERT may include a fixed-length vector that represents the input token's contextual relationships that suitable for downstream tasks, such as, without limitation, processes describe above. In some cases, implementing BERT for generation of representations of may include pre-training (bidirectionally) which involves one or more unsupervised tasks; for instance, and without limitation, processor 104 may be configured to execute a Masked Language Model (MLM) and a Next Sentence Prediction (NSP). In a non-limiting example, at least a portion of nucleotide sequence in each nucleotide sequence example may be randomly masked, and the model may learn to predict masked nucleotide sequence portions based on the context. NSP may train the model to predict, for example, and without limitation, whether two given subsequences logically follow each other. Additionally, BERT may be fine-tuned to adapt pre-trained representations. In some cases, fine-tuning BERT may include iteratively training BERT's parameters on structural alignment learning and/or masked language model learning with minimal adjustments required from the pre-trained model as described above; for instance, and without limitation, a loss function used for fine-turning may be represented as:

$$L = -\log\left(\frac{e^{s(correct)}}{\sum_j^n e^{s(j)}}\right)$$

Wherein L is the loss, s (correct) is the score of the correct label, and s (j) is the score of each possible label. It should be noted that other exemplary downstream tasks e.g., sentiment analysis, question answering, named entity recognition (NER), among others may be adapted and optimized based on the apparatus and methods described in this disclosure. As a person skilled in the art, upon reviewing the entirety of this disclosure, will be well versed in the model architectures, including multi-head self-attention mechanism and position-wise fully connected feed-forward network as described herein.

Still referring to FIG. 4, in some embodiments, a structural alignment task and/or process may involve performing a base embedding task to learn a relationship between two RNA sequences. RNA structural alignment may include a process that aligns multiple RNA sequences by inserting gaps between bases so that the conserved secondary structures are aligned in the same column. Structural alignment task may aim to obtain closer embeddings for bases in the same column of a reference alignment and obtain secondary structure embeddings by training based on the RNA structural alignment. An Rfam seed alignment for each family may be downloaded from Rfam as the reference structural alignment for the SAL task. A matrix z may be evaluated for a pairwise alignment of two RNA sequences and may be used as a score matrix when calculating the pairwise alignment. If Z=[z1, . . . , zn] and Z_= [z_1, . . . , z_m] denote the embedded representations output from the transformer layer for the input of two RNA sequences of length n and m, Each element ωi j in the _matrix may be defined to be a normalized inner product between zi and z_j:

$$\omega_{ij} = \frac{z_i \cdot z'_i}{\|z_i\|\|z'_i\|}$$

Still referring to FIG. 4, a loss function in the structural alignment task may be defined to increase ωi j at the matched position in the reference alignment so that a sequence alignment algorithm such as the Needleman-Wunsch algorithm produces the reference alignment.

Still referring to FIG. 4, alignment accuracy may be measured, and in turn used for training feedback, using sensitivity, positive predictive value (PPV) and/or F1 score, which may be calculated as follows. The number of true positives (TP) (or false positives [FP]) is the number of positions (i, j) in the predicted alignment that belong (or do not belong) to a reference alignment. The sensitivity of the predicted alignment is TP divided by the number of positions in the reference alignment, and the PPV is TP divided by the number of positions in the predicted alignment. The F1 score is the harmonic mean of sensitivity and PPV. Clustering accuracy was measured with the Rfam family as the true reference class. Three indices, namely, adjusted Rand index (ARI), homogeneity, and completeness, may be used to evaluate the clustering performance. ARI may be a measure of how well two types of clustering results match. ARI takes a real number from −1 to 1: if the value of ARI is −1, the two clustering results do not match at all, while a value of 1 indicates that they completely match. ARI may be defined as follows:

$$RI = \frac{TP + TN}{TP + TN + FP + FN}$$

$$E = \frac{(TP + FP)(TP + FN) + (TN + FP)(TN + FN)}{TP + TN + FP + FN}$$

$$ARI = \frac{TP + TN - E}{TP + TN + FP + FN - E}$$

where TP is the number of RNA sequences of the same Rfam family in the same predicted cluster, TN is the number of RNA sequences of a different Rfam family in different predicted clusters, FP is the number of RNA sequences of different Rfam families in the same predicted cluster, and FN is the number of RNA sequences of the same Rfam family in different predicted clusters. Homogeneity is a measure of the proportion of RNA sequences of a single Rfam family that belong to a single predicted cluster, and completeness measures the proportion of RNA sequences of a particular Rfam family that are assigned to the same predicted cluster.

Further referring to FIG. 4, alternative or additional structural alignment may be used, including Sankoff-style algorithms for structural pairwise alignment that simultaneously predict optimal alignment and the consensus secondary structure. For example, Dynalign and Foldalign may use thermodynamic models to find minimum free energy consensus structures. As a further example, PARTS may use a probabilistic model based on pseudo-energy obtained from base-pairing probabilities and alignment probabilities to find a most likely structural alignment. As a further non-limiting example, PMcomp may use base-pairing probability matrices generated using Mccaskill's algorithm as inputs and incorporate energy information of each sequence into these matrices to quickly find common secondary structures and alignments. LocARNA may be based on PMComp. As a further example, SPARSE may take further advantage of sparsity based on conditional probabilities of bases and base pairs in a loop region of a RNA secondary structure. RAF may utilize sparseness of alignment candidates. DAFS is a structural alignment program utilizing integer programming technique R-Coffee is a multiple RNA alignment-scoring scheme that incorporates secondary structure information. TOPAS is a network-based scheme for pairwise structural alignment of RNAs that can handle pseudoknots. TOPAS employs graph data structures to represent the RNA secondary structure including pseudoknots and designs an efficient algorithm to calculate an alignment of two graph structures by matching two nodes in two different graphs. MAFFT v7 uses Kimura's two-parameter model as a score matrix.

Still referring to FIG. 4, another evaluation test useable to measure suitability of outputs for tuning and/or error function calculation may include RNA family clustering. A similarity measure between two RNA sequences with respect to soft symmetric alignment may be defined as follows. Let $Z=[z1, \ldots, zn]$ and $Z\_=[z\_1, \ldots, z\_m]$ denote the embedded representations output from the transformer layer for the input of a pair of RNA sequences of length n and m. The similarity § between the two RNA sequences is defined to be the weighted sum of the normalized inner product between all zi and z_j pairs:

$$\hat{s} = \frac{1}{A}\sum_{i=1}^{n}\sum_{j=1}^{m}a_{ij}\omega_{ij}$$

where $$\omega_{ij} = \frac{z_i \cdot z_i'}{\|z_i\|\|z_i'\|}, A = \sum_{i=1}^{n}\sum_{j=1}^{m}a_{ij}$$

$$a_{ij} = \alpha_{ij} + \beta_{ij} - \alpha_{ij}\beta_{ij}, \alpha_{ij} = \frac{e^{\omega_{ij}}}{\sum_{k=1}^{m}e^{\omega_{ik}}}, \beta_{ij} = \frac{e^{\omega_{ij}}}{\sum_{k=1}^{m}e^{\omega_{kj}}}$$

The similarity § may be calculated for all pairs of ncRNA sequences to be clustered, and a classification matrix of size N×N is created, where N is the number of RNA sequences in the test dataset. Spectral clustering may be applied to rows of a classification matrix by considering each row of the N-dimensional vector a cluster indicator. Alternative embodiment of clustering processes may include, without limitation GraphClust, EnsembleClust, and CNNclust. CNNclust may include a deep learning-based algorithm that performs supervised learning in which a RNA family class is given as a label. CNNclust may classify RNA families that are not used for training by calculating a similarity score matrix for all pairs of input sequences. GraphClust may include an unsupervised learning algorithm that does not require the RNA family class to be a label and achieves alignment-free clustering with some exceptions. GraphClust may employ a graph kernel approach to obtain feature vectors that contain both sequence and secondary structure information. Vectors representing RNA sequences are clustered with a linear time complexity over the number of sequences using a hashing technique. EnsembleClust may calculate a similarity between two ncRNAs.

With continued reference to FIG. 1, as a non-limiting example, representation generation data structure may include a RNABERT specifically trained for accurate representation of sequences and structural alignments by adapting BERT architecture as described above. In some cases, similar to natural language processing (NLP) counterpart as described herein, RNABERT may undergo a pre-training phase where RNABERT may be configured to learn and understand the "language" of RNA sequence, wherein the pre-training phase may include tasks, such as, and without limitation, MLM and sequence alignment learning (SAL) enabling the model to predict masked bases and align sequences, respectively. In one or more embodiments, SAL may identify one or more regions of similarity that may be a consequence of functional, structural, or even evolutionary relationships between a plurality of sequences. As a non-limiting example, representation generation data structure may be configured to compare plurality of sequences to find a series of individual characters or character patterns that may be in the same order in the plurality of sequences but not necessarily contiguous. Algorithms such as, without limitation, Needleman-Wunsch Algorithm (global alignment), Smith-Waterman Algorithm (local alignment), and/or the like may be implemented and adapted to train the model on the sequence alignment tasks as described herein. RNABERT may be fine-tuned on tasks-specific dataset e.g., to predict structural alignment and/or sequencing, and/or to produce embeddings that cluster phylogenetically as described above to achieve a desired model performance.

With continued reference to FIG. 4, in one or more embodiments, neural networks as described herein may include one or more Graph Neural Networks (GNNs). GNN is a class of deep learning models designed to perform one or more processing steps as described above on data such as, without limitation, nucleotide sequences and/or related data structured as one or more graphs (e.g., non-Euclidean domains). A "graph," for the purpose of this disclosure, is a data structure used to model pairwise relations between a plurality of data objects. In some embodiments, graph may be composed of a set of vertices (also called nodes) and a set of edges (or links) that connect pairs of vertices within the set of vertices. As a non-limiting example, each vertex of set of vertices may represent nucleotides (adenine, cytosine, guanine, and uracil) and each edge of set of edge may represent a bound between at least two nucleotides. This may include, but are not limited to, linear covalent bounds linking nucleotides in the sequence, hydrogen bonds that contribute to the molecule's secondary structure such as those in Watson-Crick base pairing (A-U and G-C) and other types of interactions that define the 3D structure, among others. As another non-limiting example noted above, nodes in a graph may represent secondary structures while edges may include relationships between such structures, for instance and without limitation as described above. In some embodiments, apparatus may implement one or more GNNs, wherein each GNN may be configured to update the representation of one or more nodes in graph based on features of one or more neighboring nodes and features of one or more edges connecting them. As a non-limiting example, feature vectors or embeddings associated with each node and/or edges, which may represent attributes or states of each node, such as without limitation nucleotide interactions and/or structural relationships within RNA sequences, may be propagated across a graph through message passing or neighborhood aggregation, and model may learn a representation for each node that captures both its local and global context within the graph. Each node may generate a "message" based on its current state or feature vector. In some cases, message may also incorporate one or more features of edges connecting node to its neighbors. On the other hand, each node may collect messages from its immediate neighbors and aggregates them into a single message. Exemplary aggregation may include, without limitation, sum, mean, max, and any other functions that capture different aspects of the neighborhood information. For instance, GNNs may execute an iterative neighborhood aggregation process for each node v in a given graph at each layer l of each GNN:

$$h_v^{(l+1)} = \text{COMBINE}^l(h_v^l, \text{AGGREGATE}^l(\{h_u^l : u \in N(v)\}))$$

Where $h_v^l$ is the feature vector of node v at layer l, N(v) denotes the set of neighboring nodes of node v, AGGREGATE is an aggregation function such as any aggregation function as described herein that combines the features of the neighboring nodes, and COMBINE$^l$ is a function that updates the feature vector $h_v^l$ of node v by combining its previous feature vector with the aggregated information from its neighbors.

With continued reference to FIG. 4, additionally, or alternatively, GNNs may include, without limitation, one or more Graph Convolutional Networks (GCNs) which are similar to CNNs as described herein. As a non-limiting example, in CNNs, convolutional filters slide over grid-structured data e.g., images to capture local patterns within a fixed-size neighborhood; however, GCNs apply convolutional operations over graphs with arbitrary size to aggregate information from a node's neighbors. In an embodiment, each GCN may include one or more graph convolution layer which updates features of each node by aggregating features from its neighbors and itself. In some cases, each graph convolution layer may be configured to perform a graph convolution expressed as follows:

$$h_v^{(l+1)} = \sigma(W^l \cdot \text{MEAN}(\{h_v^l\} \cup \{h_v^l : u \in N(v)\}))$$

Where $W^l$ is a learnable weight matrix at layer l, σ is a non-linear activation function (for example, and without limitation, ReLU), and MEAN aggregation function averages the features of the node v and its neighbors. It should be noted that other aggregation functions, such as, without limitation, sum, min, max, or the like can also be used. In some cases, feature aggregation may be normalized to prevent numerical instabilities. Apparatus may be configured to iteratively train GNNs to learn one or more weight parameters that minimize a loss function defined on criteria as described above, such as clustering, structural alignment, phylogenetic clustering, comparisons of predicted and experimentally determined IRES and/or nucleotide sequence activity or the like. In some cases, loss function may quantify a difference between output representations with the ground truth labels within training sets. In some cases, weight parameters may be optimized using gradient descent or variants thereof.

Figure 5:
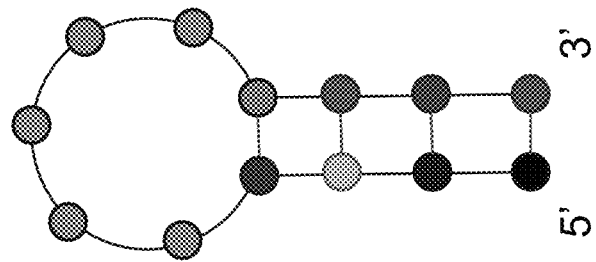
FIG. 5, a schematic diagram illustrating an exemplary embodiment of a dot-bracket notation of an RNA secondary structure.

Referring now to FIG. 5, a schematic diagram illustrating an exemplary embodiment of a dot-bracket notation of an RNA secondary structure is illustrated. A structure 504 such as a hairpin loop may include a plurality of base pairs 508, along with a plurality of non-paired elements 512 that may form a loop. Dot-bracket notation 516 may portray loops using a series of dots 520, while nucleotides that are in base pairs may be represented by brackets 524 arranged symmetrically on either side of the dots. In an embodiment, a computing device and/or processor may be configured to read dot-bracket notation and convert it to, e.g., vector and/or graph representations.

Figure 6:
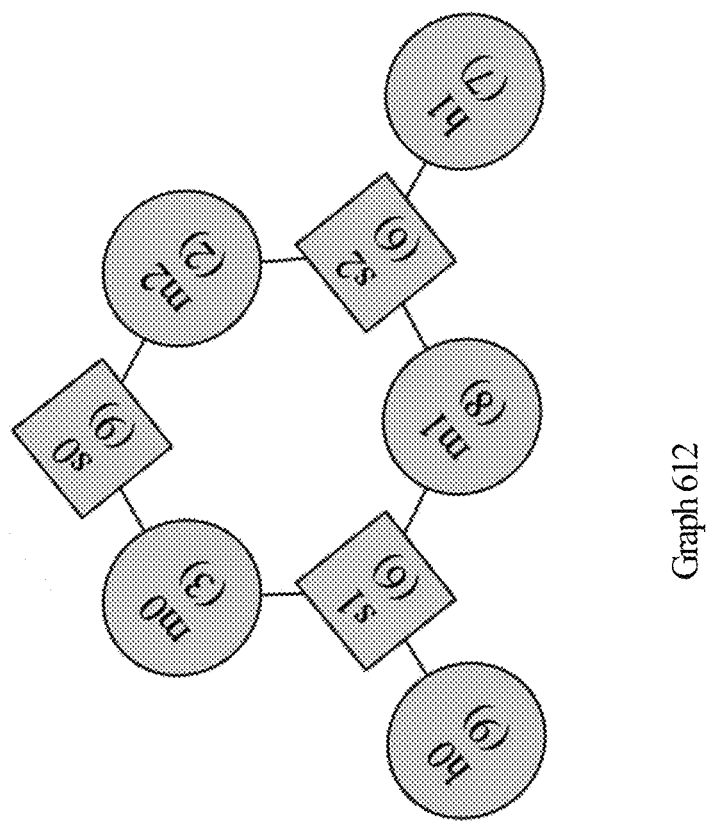
FIG. 6 is a schematic diagram illustrating an exemplary embodiment of a graph representation of an RNA secondary structure.
Figure 6:
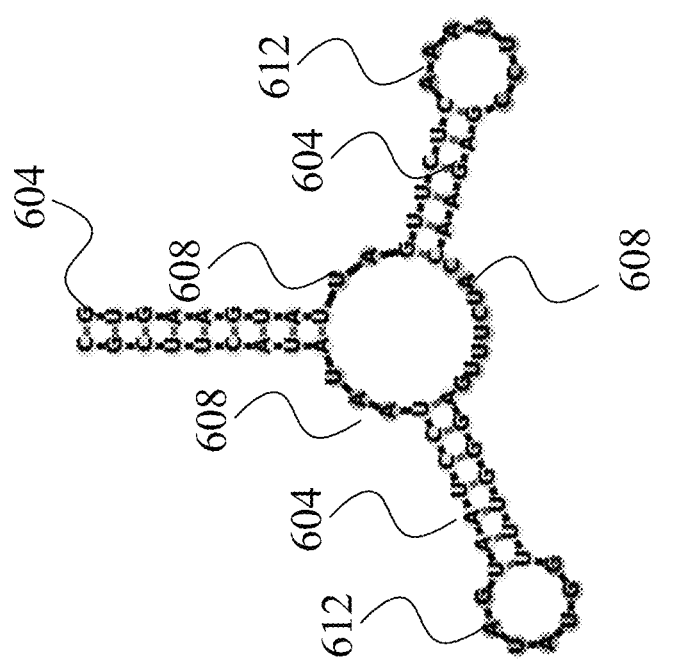

Referring now to FIG. 6, an exemplary embodiment of a graphical representation of a secondary structure 600 is illustrated. Secondary structure may include, without limitation, one or more stems 604, multiloops and/or multiloop sections 608, hairpin loops 612, and/or interior loops (not shown). Such structures may be encoded as nodes in a graph with identifiers such as textual and/or alphanumeric identifiers; for instance, a first, second, and third stem 604 structure may be identified, respectively, with labels such as "s0," "s1," and "s2," while a first, second, and third multiloop section may be identified respectively as "m0," "m1," and "m2," a first and second hairpin loop may be identified respectively as "h0" and "h1," and/or internal loops may be identified as "i0," "i1," and the like. Each such labeled representation may include one or more additional fields, such as numerical fields, representing characteristics thereof, such as a number of bas pairs in a stem, a number of nucleotides in a loop and/or loop section, or the like. Edges of a graph may represent direct connections between structural elements, such as connections from stems to multiloop sections, stems to hairpin loops, or the like; such edges may be represented alternatively or additionally using a vector per node having an element per other node, which may have a 1 or true value where a connection exists and a false or 0 value where it does not.

Figure 7:
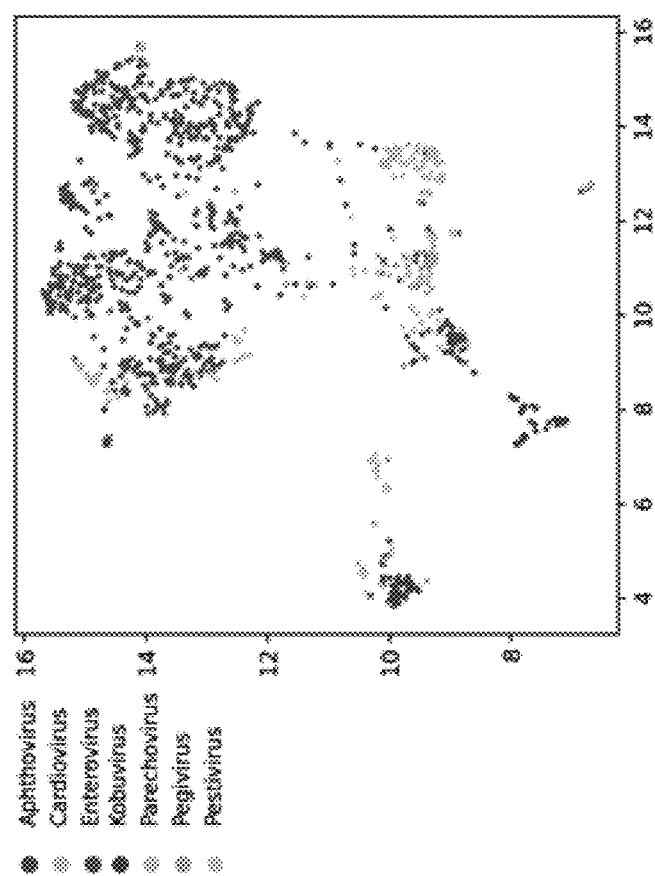
FIG. 7 is a screenshot illustrating exemplary geometric and phylogenetic clustering of representations of sequences.

Referring now to FIG. 7, a clustering result in two dimensions is illustrating showing clustering of representations and/or embeddings of nucleotide sequences, for instance as produced by representation generation data structure, where clustering according to geometric or other attributes of embeddings that are not explicitly phylogenetic results in clustering according to species of origin. Clustering may be performed and/or analyzed, without limitation, according to any process described above; in an embodiment, clustering may occur automatically via geometry of embeddings; for instance, to compare these high-dimensional mathematical representations, a dimensionality reduction method (UMap) may be utilized to map the representations onto a 2D plot, whereupon dimensionality-reduced points are then coded based on their respective phylogeny, e.g., genera. In some embodiments, a user may view coded datapoints visually to evaluate phylogenetic clustering; alternatively or additionally, a measure and/or analysis of clustering using any method described herein may be performed automatically by apparatus, and/or used as an error function for further training and/or refinement of representation generation data structure. For instance, apparatus may use methods such as k-means clustering methods or the like to identify geometric centroids of, for instance, 2-dimensionally projected datapoints and a separate set of centroids of phylogenetic clusters, and compute a distance, cosine similarity, or the like between centroids to measure a degree of phylogenetic accuracy in representations, which may in turn be used as or in an error function to retrain representation generation data structure.

Figure 8:
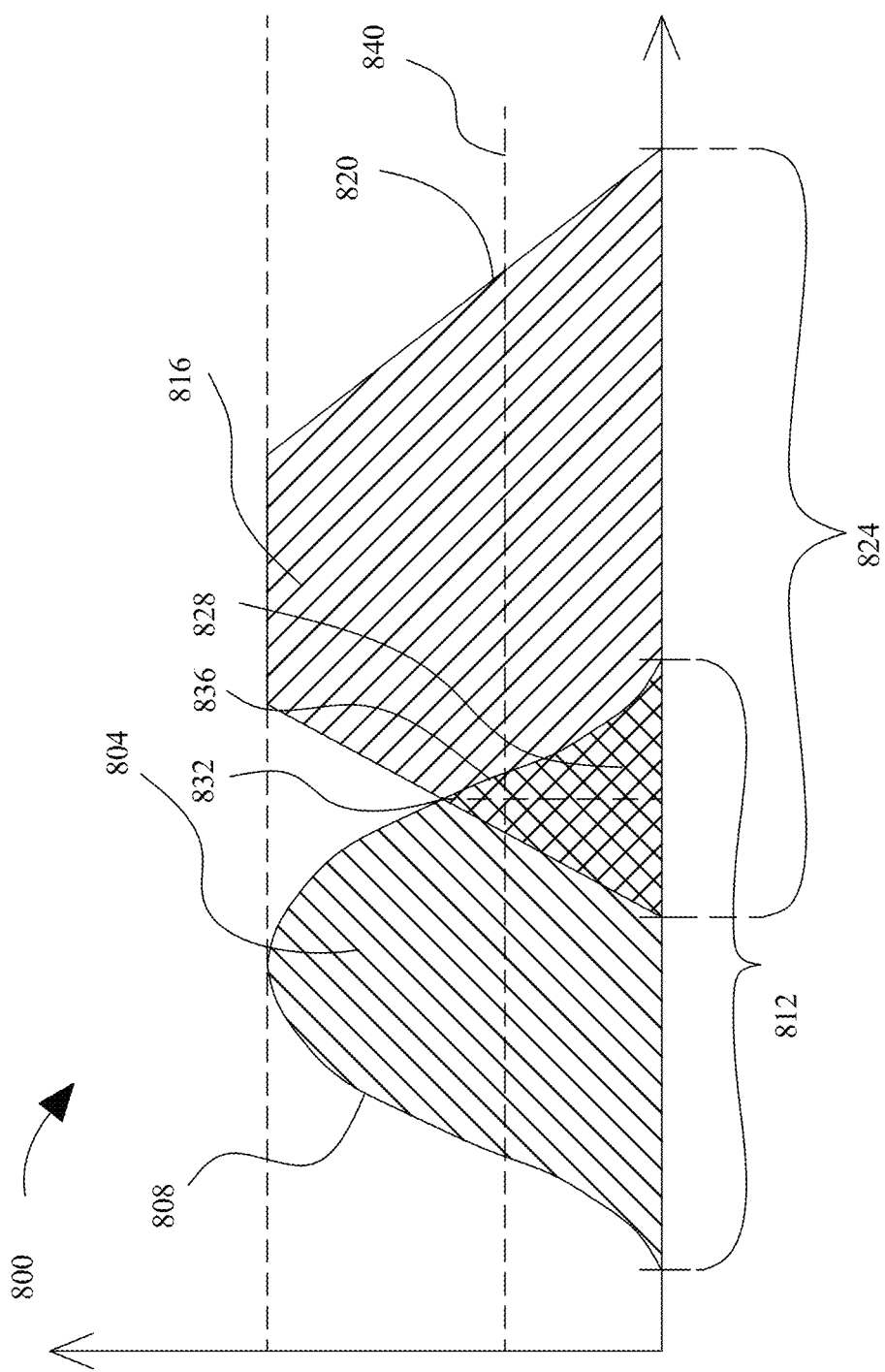
FIG. 8 is a schematic diagram illustrating an exemplary embodiment of fuzzy set comparison.

Referring to FIG. 8, an exemplary embodiment of fuzzy set comparison 800 is illustrated. A first fuzzy set 804 may be represented, without limitation, according to a first membership function 808 representing a probability that an input falling on a first range of values 812 is a member of the first fuzzy set 804, where the first membership function 808 has values on a range of probabilities such as without limitation the interval [0,1], and an area beneath the first membership function 808 may represent a set of values within first fuzzy set 804. Although first range of values 812 is illustrated for clarity in this exemplary depiction as a range on a single number line or axis, first range of values 812 may be defined on two or more dimensions, representing, for instance, a Cartesian product between a plurality of ranges, curves, axes, spaces, dimensions, or the like. First membership function 808 may include any suitable function mapping first range 812 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \dfrac{x-a}{b-a}, \text{ for } a \leq x < b \\ \dfrac{c-x}{c-b}, \text{ if } b < x \leq c \end{cases}$$

a trapezoidal membership function may be defined as:

$$y(x, a, b, c, d) = \max\left(\min\left(\dfrac{x-a}{b-a}, 1, \dfrac{d-x}{d-c}\right), 0\right)$$

a sigmoidal function may be defined as:

$$y(x, a, c) = \dfrac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\dfrac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 8, a first fuzzy set 804 may represent any value or combination of values as described above, including output from one or more machine-learning models and/or tunable data structures as described in this disclosure. A second fuzzy set 816, which may represent any value which may be represented by first fuzzy set 804, may be defined by a second membership function 820 on a second range 824; second range 824 may be identical and/or overlap with first range 812 and/or may be combined with first range via Cartesian product or the like to generate a mapping permitting evaluation overlap of first fuzzy set 804 and second fuzzy set 816.

As a non-limiting example, and continuing to refer to FIG. 6, an IRES or other activity and/or probability may be represented as one or more linguistic variables, values of which may include fuzzy sets mapping values on a continuum to logic 0 or "not active" and logic 1 or "highly active", classification to "not active," "moderately active," and "highly active," or the like. Where first fuzzy set 804 and second fuzzy set 816 have a region 828 that overlaps, first membership function 808 and second membership function 820 may intersect at a point 832 representing a probability, as defined on probability interval, of a match between first fuzzy set 804 and second fuzzy set 816. Alternatively or additionally, a single value of first and/or second fuzzy set may be located at a locus 836 on first range 812 and/or second range 824, where a probability of membership may be taken by evaluation of first membership function 808 and/or second membership function 820 at that range point. A probability at 828 and/or 832 may be compared to a threshold 840 to determine whether a positive match is indicated. Threshold 840 may, in a non-limiting example, represent a degree of match between first fuzzy set 804 and second fuzzy set 816, and/or single values therein with each other or with either set, which is sufficient for purposes of the matching process; for instance, threshold may indicate a sufficient degree of overlap between an output from at least a tunable data structure and a predetermined class and/or linguistic variable value, such as without limitation a level and/or range of IRES activity and/or probability thereof, for combination to occur as described above. Alternatively or additionally, each threshold may be tuned by a machine-learning and/or statistical process.

Further referring to FIG. 8, in an embodiment, a degree of match between fuzzy sets may be used to classify an output of tunable data structure to one or more values, levels, or probabilities of IRES activity or the like. For instance, if an output has a fuzzy set matching a fuzzy set representing a high probability of activity, by having a degree of overlap exceeding a threshold, apparatus may classify the output as belonging to the high probability and/or highly active categorization. Where multiple fuzzy matches are performed, degrees of match for each respective fuzzy set may be computed and aggregated through, for instance, addition, averaging, or the like, to determine an overall degree of match.

Still referring to FIG. 8, in an embodiment, an output may be compared to multiple fuzzy sets. For instance, in one embodiment there may be two output categorization fuzzy sets, representing respectively high IRES activity and/or probability categorization and a medium IRES activity and/or probability categorization. First categorization may have a first fuzzy set and second categorization may have a second fuzzy set Machine-learning methods as described throughout may, in a non-limiting example, generate coefficients used in fuzzy set equations as described above, such as without limitation x, c, and σ of a Gaussian set as described above, as outputs of machine-learning methods.

Further referring to FIG. 8, an inference engine may be implemented according to input and/or output membership functions and/or linguistic variables. For instance, a first linguistic variable may represent a first measurable value pertaining to IRES activity probability, while a second may pertain to a period of stability, temperature resistance, PH compatibility, or the like for an RNA sequence containing an IRES. An inference engine may combine rules, such as: 'if the probability of IRES activity is high and the stable period is "long," the IRES score is "useful"' where the output is a linguistic variable having values on a continuum from "not useful," to "moderately useful" to "highly useful." The degree to which a given input function membership matches a given rule may be determined by a triangular norm or "T-norm" of the rule or output membership function with the input membership function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T (T(a, b), c)), and the requirement that the number 1 acts as an identity element. Combinations of rules ("and" or "or" combination of rule membership determinations) may be performed using any T-conorm, as represented by an inverted T symbol or "⊥," such as max (a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score pertaining to a fuzzy set classification and/or linguistic variable value, including without limitation categorization of IRES activity and/or probability or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

Figure 9:
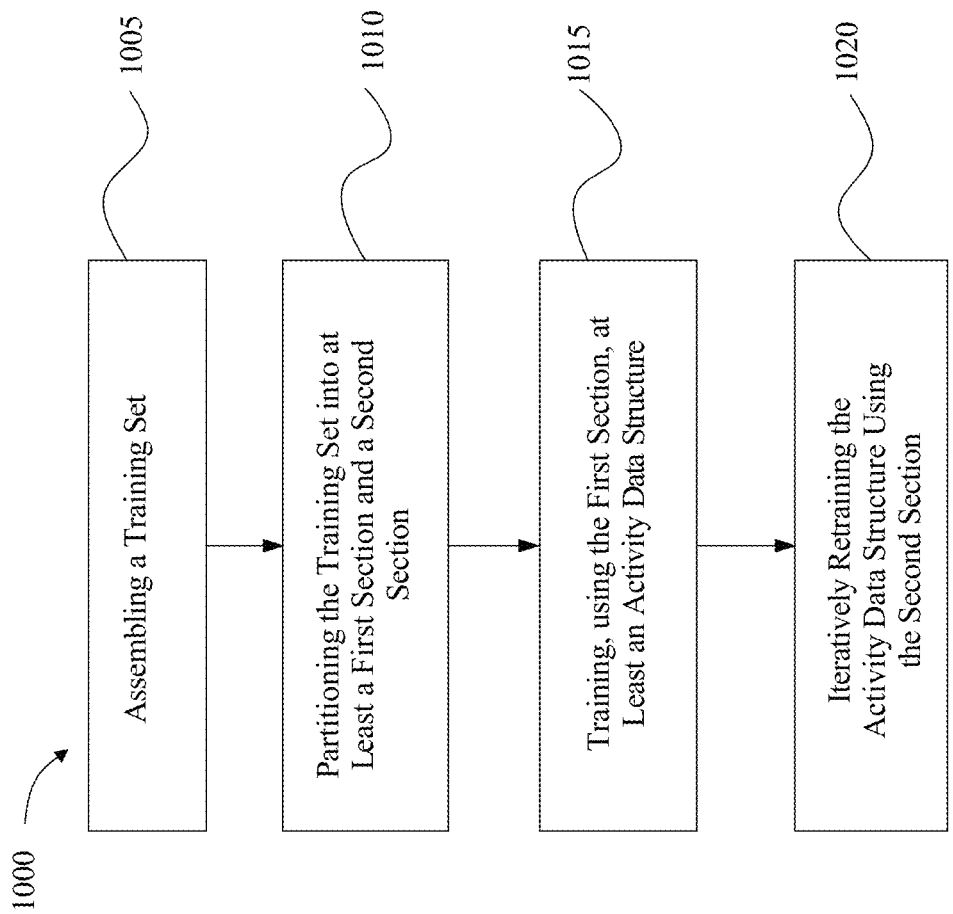
FIG. 9 is a flow diagram illustrating an exemplary embodiment of a method of training a tunable data structure to predict internal ribosome entry sites (IRES) activity.

Referring now to FIG. 9, an exemplary embodiment of a method 900 of training a tunable data structure to predict internal ribosome entry site (IRES) activity is illustrated. At step 905, an apparatus assembling a training set that includes a plurality of nucleotide sequence data examples describing a plurality of IRES sequences 160 and a plurality of correlated observed IRES activity; this may be implemented, without limitation, as described above in reference to FIGS. 1-8. Assembling the training set may include converting each IRES sequence 168 of the plurality of IRES sequences 160 into a corresponding nucleotide sequence data example of the plurality of nucleotide sequence data examples using a representation generation data structure. Representation generation data structure may include a neural network. A neural network may include a BERT neural network.

Continuing to refer to FIG. 9, in some exemplary embodiments representation generation data structure may have an input having a first sequence size. Continuing the non-limiting example, an IRES sequence 168 of the plurality of IRES sequences 160 may have a second sequence size greater than the first sequence size; converting the IRES sequence 168 to a nucleotide sequence data example of plurality of nucleotide sequence data examples may include inputting a plurality of sections of the at least one IRES sequence 168, wherein each section has a section sequence size equal to the first sequence size, outputting a plurality of sectional nucleotide sequence data outputs, aggregating the sectional nucleotide sequence data outputs, and generating the nucleotide sequence data example using the aggregated sectional nucleotide sequence data outputs; this may be implemented, without limitation, as described above in reference to FIGS. 1-8.

Still referring to FIG. 9, at step 910, apparatus partitions training set into at least a first section and a second section; this may be implemented, without limitation, as described above in reference to FIGS. 1-8.

Further referring to FIG. 9, and at step 915, apparatus trains, using the first section, at least an activity data structure 164a-m to generate probable IRES activity 172 using nucleotide sequence data; this may be implemented, without limitation, as described above in reference to FIGS. 1-8. At least an activity data structure 164a-m may include at least an activity neural network. At least an activity neural network may include a graph neural network. At least an activity neural network may include a convolutional neural network.

Still referring to FIG. 9, and at step 920, apparatus iteratively retrains at least an activity data structure 164a-m using the second section; this may be implemented, without limitation, as described above in reference to FIGS. 1-8. Each iteration of iterative retraining includes generating a predicted IRES activity value using the at least an activity neural network and a nucleotide sequence data example, evaluating an error function using the predicted IRES activity value and an observed IRES activity correlated to the nucleotide sequence data example, and tuning the at least an activity data structure 164a-m using the evaluated error function.

With continued reference to FIG. 9, at least an activity data structure 164a-m may include a plurality of activity data structures 156a-m. Apparatus may generate, for each activity data structure 164a-m of the plurality of activity data structures 156a-m, at least an efficacy metric. Apparatus may select an activity data structure 164a-m of the plurality of activity data structures 156a-m as a function of the at least an efficacy metric.

Further referring to FIG. 9, a non-transitory machine-readable medium may include instructions configured to cause a computing device and/or at least a processor to perform any or all method steps as disclosed above, in any order or with any number of repetitions. Generally speaking, a computer-accessible medium may include any tangible or non-transitory storage media or memory media such as electronic, magnetic, or optical media—e.g., disk or CD/DVD-ROM coupled to computer system via a bus. The terms "tangible" and "non-transitory," as used herein, are intended to describe a computer-readable storage medium (or "memory") excluding propagating electromagnetic signals but are not intended to otherwise limit the type of physical computer-readable storage device that is encompassed by the phrase computer-readable medium or memory. For instance, the terms "non-transitory computer-readable medium" or "tangible memory" are intended to encompass types of storage devices that do not necessarily store information permanently, including for example, random access memory (RAM). Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

The terms "tangible" and "non-transitory," as used herein, are intended to describe a computer-readable storage medium (or "memory") excluding propagating electromagnetic signals, but are not intended to otherwise limit the type of physical computer-readable storage device that is encompassed by the phrase computer-readable medium or memory. For instance, the terms "non-transitory computer readable medium" or "tangible memory" are intended to encompass types of storage devices that do not necessarily store information permanently, including for example, random access memory (RAM). Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

The term "non-transitory," as used herein, is a limitation of the medium itself (i.e., tangible, not a signal) as opposed to a limitation on data storage persistency (e.g., RAM vs. ROM). Non-transitory memory may include computer memory that has input-independent persistence across at least one clock cycle of a synchronous system and/or may be read-enabled or write-enabled and maintains its stored value when not write-enabled and when inputs have been changed not to match its stored value for at least one read cycle. I.e., could include capacitive memory, latches, or the like.

A non-transitory machine-readable medium may include instructions configuring a computing device and/or at least a processor to assemble a training set, the training set including a plurality of nucleotide sequence data examples describing a plurality of IRES sequences 160 and a plurality of correlated observed IRES activity, partition the training set into at least a first section and a second section, train at least an activity data structure 164a-m to generate probable IRES activity 172 using nucleotide sequence data, and iteratively retrain the at least an activity data structure 164a-m using the second section. Each iteration of the iterative retraining further includes generating a predicted IRES activity value using the at least an activity neural network and a nucleotide sequence data example, evaluating an error function using the predicted IRES activity value and an observed IRES activity correlated to the nucleotide sequence data example, and tuning the at least an activity data structure 164a-m using the evaluated error function.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
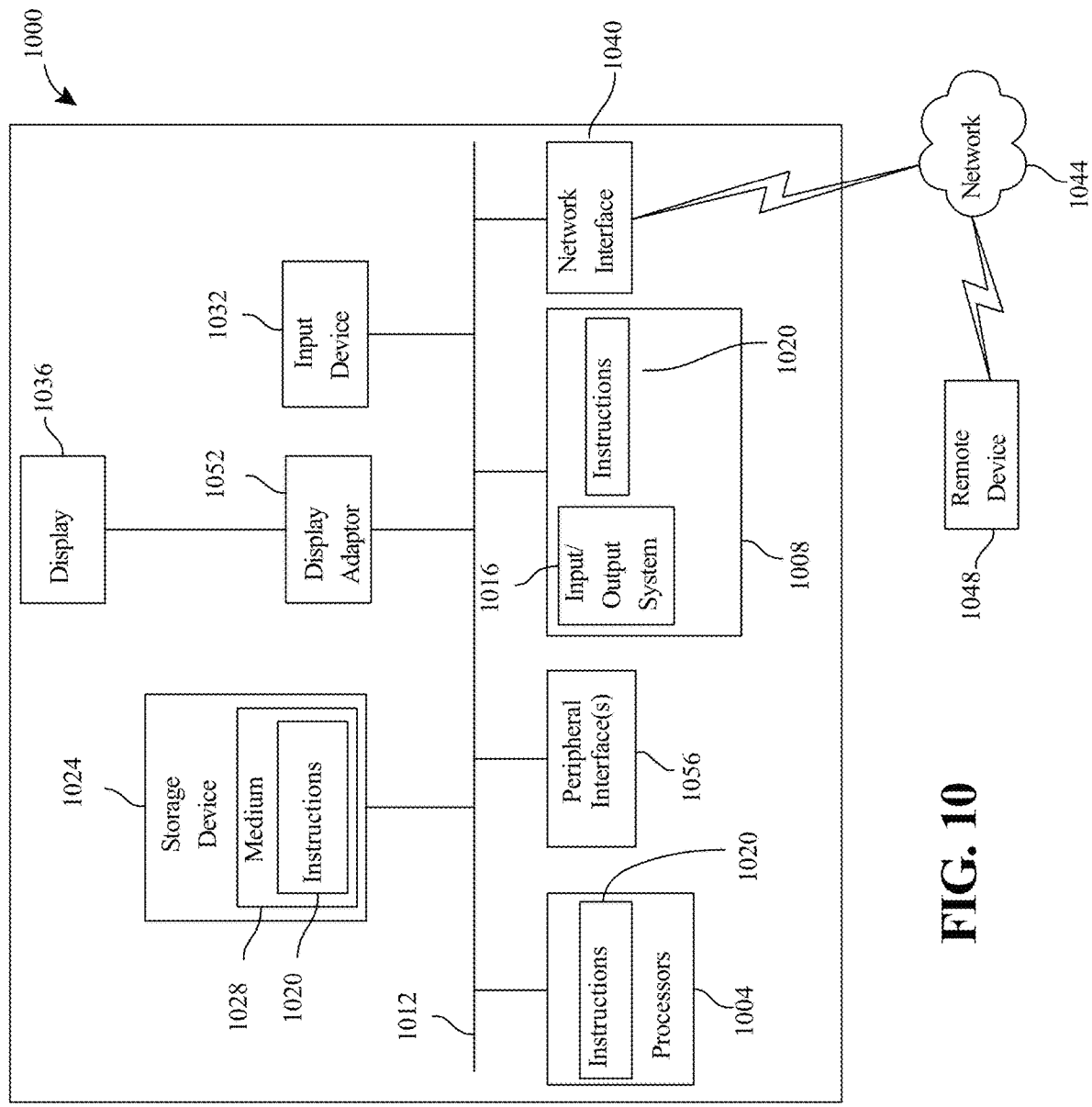
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for training a tunable data structure to predict internal ribosome entry site (IRES) activity, the apparatus comprising:
   at least a processor; and
   a memory communicatively connected to the at least a processor, the memory containing instructions configuring the at least a processor to:
   assemble a training set, the training set comprising a plurality of nucleotide sequence data examples describing a plurality of IRES sequences and a plurality of correlated observed IRES activity, wherein:
   assembling the training set further comprises converting each IRES sequence of the plurality of IRES sequences into a corresponding nucleotide sequence data example of the plurality of nucleotide sequence data examples using a representation generation data structure;
   the representation generation data structure has an input having a first sequence size;
   an IRES sequence of the plurality of IRES sequences has a second sequence size greater than the first sequence size; and
   converting the IRES sequence to a nucleotide sequence data example of the plurality of nucleotide sequence data examples further comprises:
   inputting a plurality of sections of the IRES sequence, wherein each section has a section sequence size equal to the first sequence size;
   outputting a plurality of sectional nucleotide sequence data outputs;
   aggregating the sectional nucleotide sequence data outputs; and
   generating the nucleotide sequence data example using the aggregated sectional nucleotide sequence data outputs;

partition the training set into at least a first section and a second section;

train, using the first section, at least an activity data structure to generate probability of IRES activity using nucleotide sequence data; and iteratively retrain the at least an activity data structure using the second section, wherein each iteration of the iterative retraining further comprises:

generating a predicted IRES activity value using the at least an activity data structure and a nucleotide sequence data example;

evaluating an error function using the predicted IRES activity value and an observed IRES activity correlated to the nucleotide sequence data example; and tuning the at least an activity data structure using the evaluated error function.

2. The apparatus of claim 1, wherein the representation generation data structure further comprises a neural network.

3. The apparatus of claim 2, wherein the neural network further comprises a bidirectional encoder representations from transformer (BERT) neural network.

4. The apparatus of claim 1, wherein the at least an activity data structure further comprises at least an activity neural network.

5. The apparatus of claim 4, wherein the at least an activity neural network further comprises a graph neural network.

6. The apparatus of claim 4, wherein the at least an activity neural network further comprises a convolutional neural network.

7. The apparatus of claim 1, wherein the at least an activity data structure further comprises a plurality of activity data structures, and further comprising:

generating, for each activity data structure of the plurality of activity data structures, at least an efficacy metric; and selecting an activity data structure of the plurality of activity data structures as a function of the at least an efficacy metric.

8. The apparatus of claim 7, wherein each activity data structure of the plurality of activity data structures is trained with a distinct training data partition.

9. A method of training a tunable data structure to predict internal ribosome entry site (IRES) activity, the method comprising:

assembling, by a computing device, a training set, the training set comprising a plurality of nucleotide sequence data examples describing a plurality of IRES sequences and a plurality of correlated observed IRES activity, wherein:

assembling the training set further comprises converting each IRES sequence of the plurality of IRES sequences into a corresponding nucleotide sequence data example of the plurality of nucleotide sequence data examples using a representation generation data structure;

the representation generation data structure has an input having a first sequence size;

an IRES sequence of the plurality of IRES sequences has a second sequence size greater than the first sequence size; and converting the IRES sequence to a nucleotide sequence data example of the plurality of nucleotide sequence data examples further comprises:

inputting a plurality of sections of the IRES sequence, wherein each section has a section sequence size equal to the first sequence size;

outputting a plurality of sectional nucleotide sequence data outputs;

aggregating the sectional nucleotide sequence data outputs; and generating the nucleotide sequence data example using the aggregated sectional nucleotide sequence data outputs;

partitioning the training set into at least a first section and a second section;

training, using the first section, at least an activity data structure to generate probability of IRES activity using nucleotide sequence data; and iteratively retraining the at least an activity data structure using the second section, wherein each iteration of the iterative retraining further comprises:

generating a predicted IRES activity value using the at least an activity neural network and a nucleotide sequence data example;

evaluating an error function using the predicted IRES activity value and an observed IRES activity correlated to the nucleotide sequence data example; and tuning the at least an activity data structure using the evaluated error function.

10. The method of claim 9, wherein the representation generation data structure further comprises a neural network.

11. The method of claim 10, wherein the neural network further comprises a bidirectional encoder representations from transformer (BERT) neural network.

12. The method of claim 9, wherein the at least an activity data structure further comprises at least an activity neural network.

13. The method of claim 12, wherein the at least an activity neural network further comprises a graph neural network.

14. The method of claim 12, wherein the at least an activity neural network further comprises a convolutional neural network.

15. The method of claim 9, wherein the at least an activity data structure further comprises a plurality of activity data structures, and further comprising:

generating, for each activity data structure of the plurality of activity data structures, at least an efficacy metric; and selecting an activity data structure of the plurality of activity data structures as a function of the at least an efficacy metric.

16. A non-transitory machine-readable medium containing instructions configured to cause at least a processor to:

assemble a training set, the training set comprising a plurality of nucleotide sequence data examples describing a plurality of IRES sequences and a plurality of correlated observed IRES activity, wherein:

assembling the training set further comprises converting each IRES sequence of the plurality of IRES sequences into a corresponding nucleotide sequence data example of the plurality of nucleotide sequence data examples using a representation generation data structure;

the representation generation data structure has an input having a first sequence size;

an IRES sequence of the plurality of IRES sequences has a second sequence size greater than the first sequence size; and converting the IRES sequence to a nucleotide sequence data example of the plurality of nucleotide sequence data examples further comprises:
  inputting a plurality of sections of the IRES sequence, wherein each section has a section sequence size equal to the first sequence size;
  outputting a plurality of sectional nucleotide sequence data outputs;
  aggregating the sectional nucleotide sequence data outputs; and
  generating the nucleotide sequence data example using the aggregated sectional nucleotide sequence data outputs;
partition the training set into at least a first section and a second section;
train at least an activity data structure to generate probable IRES activity using nucleotide sequence data; and
iteratively retrain the at least an activity data structure using the second section, wherein each iteration of the iterative retraining further comprises:
  generating a predicted IRES activity value using the at least an activity neural network and a nucleotide sequence data example;
  evaluating an error function using the predicted IRES activity value and an observed IRES activity correlated to the nucleotide sequence data example; and
  tuning the at least an activity data structure using the evaluated error function.

* * * * *